US007404221B2

(12) United States Patent
Sackner

(10) Patent No.: US 7,404,221 B2
(45) Date of Patent: *Jul. 29, 2008

(54) RECIPROCATING MOVEMENT PLATFORM FOR THE EXTERNAL ADDITION OF PULSES TO THE FLUID CHANNELS OF A SUBJECT

(75) Inventor: Marvin A. Sackner, Miami, FL (US)

(73) Assignee: Non-Invasive Monitoring Systems, Inc., Miami, FL (US)

( * ) Notice: Subject to any disclaimer, the term of this patent is extended or adjusted under 35 U.S.C. 154(b) by 0 days.

This patent is subject to a terminal disclaimer.

(21) Appl. No.: 10/566,872

(22) PCT Filed: Aug. 4, 2004

(86) PCT No.: PCT/US2004/025017

§ 371 (c)(1), (2), (4) Date: Feb. 2, 2006

(87) PCT Pub. No.: WO2005/016216

PCT Pub. Date: Feb. 24, 2005

(65) Prior Publication Data

US 2006/0185083 A1 Aug. 24, 2006

Related U.S. Application Data

(63) Continuation-in-part of application No. 10/439,957, filed on May 15, 2003, now Pat. No. 7,111,346.

(60) Provisional application No. 60/492,451, filed on Aug. 4, 2003.

(51) Int. Cl.
*A61B 5/00* (2006.01)
*A61G 7/00* (2006.01)

(52) U.S. Cl. ...................... 5/600; 5/109; 5/648; 601/24

(58) Field of Classification Search ..................... 5/108, 5/109, 624, 648–651; 128/845, 882; 601/24, 601/51, 98, 116, 49
See application file for complete search history.

(56) References Cited

U.S. PATENT DOCUMENTS

| | | | | | |
|---|---|---|---|---|---|
| 2,641,252 | A * | 6/1953 | Hemming | 601/98 |
| 2,856,916 | A * | 10/1958 | Gilbert | 601/98 |
| 3,455,297 | A * | 7/1969 | Russell | 601/98 |
| 3,532,089 | A * | 10/1970 | Arntzenius | 601/51 |
| 3,654,918 | A * | 4/1972 | Blok et al. | 601/98 |
| 6,106,491 | A | 8/2000 | Gianutsos | |
| 6,155,976 | A * | 12/2000 | Sackner et al. | 600/300 |
| 7,111,346 | B2 * | 9/2006 | Inman et al. | 5/600 |

* cited by examiner

*Primary Examiner*—Michael Trettel
(74) *Attorney, Agent, or Firm*—Cohen Pontani Lieberman & Pavane LLP

(57) ABSTRACT

An apparatus comprising a mattress, a mattress support, cast shoes, a footboard support, a drive for causing the reciprocating movement, and a box frame to contain and support the reciprocating movement platform is disclosed. The apparatus provides medical treatments, which are also described, by externally applying periodic acceleration to the body of a subject on the mattress.

83 Claims, 8 Drawing Sheets

FIG. 3A
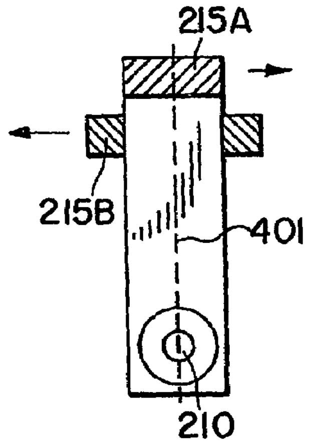
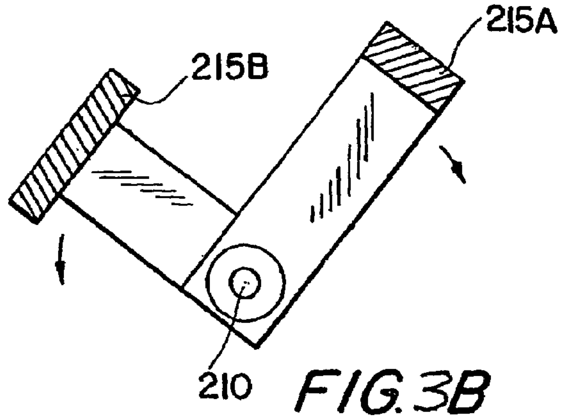
FIG. 3B
FIG. 3C
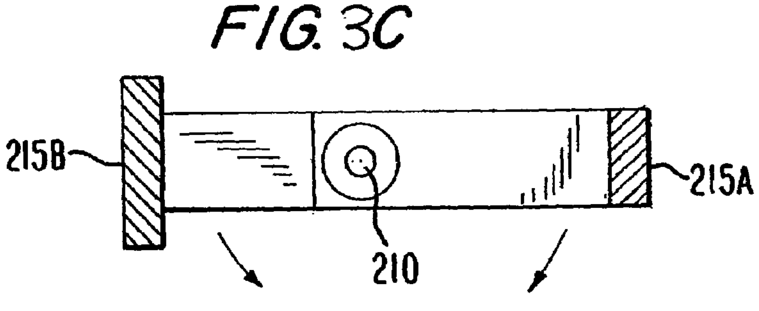
FIG. 3D
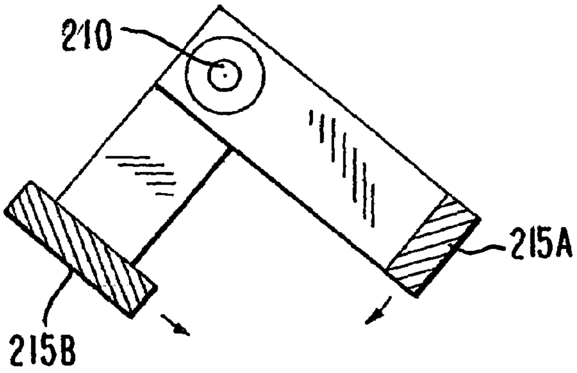
FIG. 3E
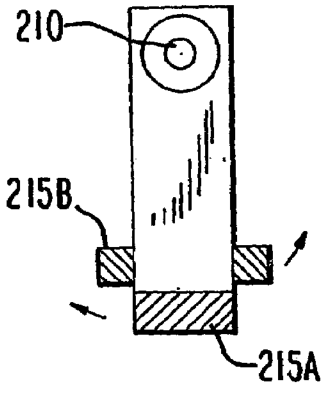

RECIPROCATING MOVEMENT PLATFORM FOR THE EXTERNAL ADDITION OF PULSES TO THE FLUID CHANNELS OF A SUBJECT

CROSS REFERENCES TO RELATED APPLICATIONS

This application claims priority from U.S. Provisional Patent Application Ser. No. 60/492,451 which was filed on Aug. 4, 2003 and is hereby incorporated in its entirety, and this application is a continuation-in-part of U.S. Non-Provisional patent application Ser. No. 10/439,957, which was filed on May 15, 2003 (now issued as U.S. Pat. No. 7,111,346) and is also incorporated in its entirety.

BACKGROUND OF THE INVENTION

1. Field of the Invention

The present invention relates generally to a reciprocating motion platform for oscillating a subject in a back and forth, headward to footward manner in order to externally add pulses to the fluid channels of the subject. The external addition of pulses caused by the periodic acceleration of the subject results in many therapeutic benefits.

2. Description of the Related Art

This application builds on the work previously done in this field by Non-Invasive Monitoring Systems, Inc., located at 1666 Kennedy Causeway, Suite 400 in North Bay Village, Fla., as exemplified in U.S. Pat. No. 6,155,976 to Sackner et al. entitled "Reciprocating Movement Platform For Shifting Subject To and Fro in Headwards-Footwards Direction" (hereinafter referred to as the '976 patent), U.S. patent application Ser. No. 09/967,422 (U.S. Patent Application Publication Serial No. 2002/0103454) filed by Dr. Marvin Sackner and D. Michael Inman, entitled "External Addition of Pulses To Fluid Channels Of Body To Release Or Suppress Endothelial Mediators And To Determine Effectiveness Of Such Intervention" (hereinafter referred to as the '454 publication), and U.S. patent application Ser. No. 10/439,957 (U.S. Patent Application Publication Serial No. 2003/0236476), filed by Dr. Marvin Sackner and D. Michael Inman, entitled "Reciprocating Movement Platform For The External Addition of Pulses of The Fluid Channels of a Subject", (hereinafter referred to as the '957 application). All of the '976 patent, the '454 publication, and '957 application are hereby incorporated by reference.

Both the '976 patent and the '957 application describe reciprocating movement platforms which can be used in medical treatments based on the external addition of pulses, as well as various medical treatments based on the external addition of pulses. The '454 publication is directly mostly to medical treatments. Although the present application builds on these three works, it is not limited by them.

Although the three works are incorporated by reference, a description of one embodiment of a reciprocating movement platform in the '957 application is presented below to provide a background by which to understand the present invention. The placement of this description in the background section does not mean to suggest by any means that the applicant considers or admits that the '957 application is necessarily prior art to the present application. Its placement here is merely to demarcate the material disclosed in the '957 application from the new material described herein.

The '957 application described one embodiment of a reciprocating movement platform as shown in FIGS. 1, 4, 5, and 6. FIGS. 1, 4, 5, and 6 show a completely constructed reciprocating movement platform comprised of a mattress 101 for the subject to lie upon, a pillow 102 for the subject's head, a footboard frame 103 with cast shoes 104 attached in order to secure the subject, a mattress support 105 to hold the mattress 101 and to which the footboard frame 103 is attached, a box frame 800 which holds the drive machinery (or "drive") 200 onto which the mattress support 105 is attached, bumpers 820 attached to the top and bottom of the box frame 800, and casters 830 at the four corners of the bottom of the box frame 800 for moving the reciprocating movement platform.

The entire reciprocating movement platform system (without patient, i.e., mattress 101 and mattress support 105, footboard support 105, box frame 800, and drive machinery 200) weighs between 400 and 500 lbs. The entire reciprocating movement platform system is 30" wide, which is the standard width of a hospital gurney, so that it may be easily moved through doorways, semi-crowded offices, etc. The length of the entire system from bumper to bumper is 88", which is as long as a standard twin or king size bed. The mattress 101 is 30" above the floor, and the top of the footboard support 103 is 42" above the floor.

The mattress support 105 secures the mattress 101 by means of Velcro strips. The mattress support 105 and footboard support 105 together weigh roughly 120 lbs. total. When assembled, the combined mattress support 105 and footboard support 105 are 30" wide and 82" long. The mattress 101 is 6" thick, 30" wide, 80" long, and weighs approximately 30 lbs. The top 3" of the mattress foam is the "visco-elastic" type foam for form-fitting comfort while the subject is on the platform. The mattress 101 can be designed to fold in half for easier transport and storage.

FIG. 7 shows the cast shoes 104 and the footboard frame 103 to which they are attached. The cast shoes 104 of the footboard frame 103 are the only means by which the subject is secured to the mattress support 105, and thus, is the means by which the subject is "pulsed" by the reciprocating platform. The two cast shoes 104 are rigidly attached by nuts and bolts to the footboard frame 103. Once the subject is lying on the mattress 101, he or she will put his or her feet (with shoes on) into the cast shoes 104 and then the cast shoes 104 will be secured around the shoes by a system of Velcro and straps and cloth. Experiments have shown that "one size fits many", with the cast shoes 104 servicing most adults quite adequately due to the flexibility of the Velcro closure system. The feet may be fastened in the cast shoes 104 by other means, such as a ski boot-like apparatus, or another fastening means, such as a snap, a buckle, a lock, etc. connection.

The casters 830 on the bottom portion of the reciprocating movement platform are 6" hospital bed casters with central locking features; these provide easy rolling and maneuvering, good ground clearance, easy locking (as shown by the brake petal), and an attractive appearance. The ground clearance is approximately 8", which accommodates the use of equipment (such as hoists) to lift the reciprocating movement platform. The bumpers 820 make sure the reciprocating platform is not set too close to a wall by extending further out than the mattress support 105. The mattress support 105 is 82" long and, when the platform is engaged in a reciprocating movement, has a range of movement of +/−2". The bumpers 820 are built to extend 1" beyond the furthest limit the mattress support 105 can travel so that the reciprocating movement platform will not be accidentally set too close to a wall where it might bump the wall during operation.

The drive machinery (or "drive") 200 is enclosed within the box frame 800 and, as such, cannot be seen from the outside of the fully assembled movement platform. Supported by the box frame 800 and attached to the mattress support 105, the drive 200 provides the reciprocating movement of the device.

The reciprocating (headwards-footwards) movement preferably has a rate of about 120-180 rpm with a force in the range of about +/−0.2 to about +/−0.3 g. The relationship between the parts can be seen in the exploded view of the reciprocating movement platform shown in FIG. 1. Starting from the top, the mattress 101 attaches to the mattress support 105 with Velcro strips, while the footboard frame 103 (with attached cast shoes 104) is bolted onto the mattress support 105. The mattress support 105 is securely attached to the drive 200. The drive 200 has four track wheels 232 located in the four top corners of the drive 200. These wheels 232 sit in four similarly placed tracks in the box frame 800. Hence, the drive 200, mattress support 105, and mattress 101 form one part of the assembled movement platform, and the only physical connection between this top part and the bottom box frame 800 is the four wheels 232 of the drive 200 sitting in the four tracks of the box frame 800.

When the drive 200, by means which will be discussed further below, moves within the box frame 800, the wheels 232 move within the tracks, which serve to both support the drive 200 and limit the reciprocating motion of the drive 200. The track 810 on top of the box frame 800 has rounded ends so that the wheel 232 of the drive 200 may only move a certain distance in either direction. The track is beveled so that the track wheel 232 of the drive 200 will rest naturally in the center of the track. The track is also located near the metal support struts of the box frame 800 which thus transfer the weight of the drive 200 (and the attached mattress support 105, mattress 101, and subject) directly down to the caster 830 in the corner below.

The box frame 800 weighs about 120 lbs. and serves at least the following five purposes: 1) supporting the rest of the platform (the drive 200, mattress support 105, mattress 101, and subject); 2) providing a foundation that can be moved or anchored by means of the casters 830; 3) maintaining an adequate distance from surrounding walls by means of its bumpers 820; (4) carrying the system electronics; and (5) encasing the drive 200 for safety and noise reduction. In addition, the box frame 800 provides ground clearance for the hoist legs.

The drive 200 weighs 200 lbs and is 24" wide. The displacement modules in the drive 200 take the form of two pairs of rotating counterweights, connecting belts, pulleys, springs, and motors. FIGS. 2A and 2B are drawings of a side view and a top view, respectively, of the drive 200 and its various mechanisms. In FIGS. 2A and 2B, the two pairs of drive weights 215A & 215B and 225A & 225B are shown attached to their respective horizontal shafts 210 and 220. These shafts are attached by means of struts to the frame of the drive 200. The four track wheels 232 can be seen in FIGS. 2A-2B. There are two motors, the drive rotation motor 1700 which drives the drive weights and a linear displacement motor 260 which sets the phase difference between the two pairs of drive weights. The drive rotation motor 1700 is a 180VDC ½ hp 0-1750 RPM motor, although only ⅒ hp is actually used. The linear displacement motor 260 is a 9" per minute 400 lb. 110VAC linear displacer with 12" of travel.

The movement of counterweights 215A and 215B as seen from above is shown in FIGS. 3A-E. In FIG. 3A, the centers of gravity of both drive weights 215A and 215B are on the same line 401 from center drive shaft 210. As center drive shaft 210 continues to rotate in FIG. 3B, drive weights 215A and 215B continue their rotations in opposite directions: drive weight 215A in a clockwise direction, drive weight 215B in a counter-clockwise direction. In FIG. 3C, the drive weights have moved into positions opposite each other. This is beneficial because the force of the two drive weights are also in opposite directions and thus, negate each other's effect. The rotation continues in FIG. 3D and then the drive weights end up adding the force of their weights in the same direction in FIG. 3E. FIGS. 3A-E show how the motion of the drive weights moves the drive 200 up and down the box frame tracks (i.e., headwards and footwards for a subject on the mattress 101), but not sideways within the box frame 800. If FIG. 3A is the position which causes the headward movement, FIG. 3C is the position which negates any movement, and FIG. 3E causes the footward movement.

As can be seen in FIGS. 2A-2B and 3A-3E, the drive weights are of unequal size. This is because the weights are located at different distances from the center of drive shaft 210. If the drive weights were the same mass, their effects would not be balanced and the drive 200 would rock sideways in the box frame 800. However, if drive weight 215B is a predetermined amount of mass less than drive weight 215A, the effect of the drive weights when rotating in opposite directions will cancel each other out. Because of this arrangement, the drive weights are in the same horizontal plane as shown in FIG. 2, which greatly reduces any shimmy effect that was produced in previous platform versions which had their drive weights in different horizontal planes. The outer edge of drive weight 215A is 12" from drive shaft 210 and this outer edge travels past the very outside edge of the drive itself when rotating.

FIG. 2B shows the pulley system with drive belt 370 and the phase control belt 380. The drive belt 370 runs from drive rotation motor 1700 to drive shaft 210 and provides the power to rotate drive weights 215A and 215B around drive shaft 210 and indirectly provides the power to rotate drive weights 225A and 225B around shaft 220. Drive belt 370 is a ¾" L pitch timing belt, although a timing belt is not required in this position. Because of the size of the wheel around drive shaft 210 which is driven by drive belt 370 in comparison to the size of rotation shaft, there is a 5:1 speed reduction from the drive rotation motor 1700 to the actual rotational speed of the drive weights.

Phase control belt 380 runs around four pulley wheels of equal size: a release pulley wheel, a drive shaft pulley wheel, secondary shaft pulley wheel, and a linear displacement pulley wheel. Because it is also attached to drive shaft 210, the drive pulley wheel drives the phase control belt. Secondary shaft pulley wheel receives the power to rotate the drive weights around shaft 220 from the drive shaft pulley wheel through phase control belt 380. The release pulley wheel provides required tension for phase control belt 380, and can also be used to release the tension on phase control belt 380 in order that phase control belt 380 can be taken off for repair or transport. Linear displacement pulley wheel can be moved in position up and down linear shaft under the control of linear displacement motor 260. It is by this means that the relative phases of the two pairs of drive weights are controlled.

The drive weights around each shaft make the same movements as shown in FIGS. 3A-3E. However, one pair of drive weights can be moved in and out of phase with the other pair of drive weights. The two pairs of drive weights are in phase when they are in the same rotational positions at the same time. Both pairs would look like FIG. 3A at the same time, like FIG. 3B at the same time, etc. The two pairs are out of phase when they are not in the same rotational positions at the same time. For instance, drive weights 215A & 215B might be in the position shown in FIG. 3A, while drive weights 225A & 225B might be in the positions shown in FIG. 3B. In that case, they would be 45° out of phase with each other. Although the sideways forces of these out-of-phase pairs of drive weights would still cancel themselves out (and thus not produce a rocking effect in the movement platform), the force produced in the headwards-footwards directions would lessen in comparison to when the pairs of drive weights are in phase.

The relative phases of the pairs of drive weights are controlled by the linear displacement motor 360, which controls the pulley system. The speed of rotation of the pairs of drive weights are controlled by increasing or decreasing the speed of the drive rotation motor 1700. Thus, one can control both the speed of the headwards-footwards movement (by increasing or decreasing the speed of the drive rotation motor 1700) and the force applied by the headwards-footwards movement (by moving the pairs of drive weights in and out of phase with each other through linear displacement pulley wheel under the control of linear displacement motor 360). In its simplest form, the control electronics of the present invention merely control these two variables in order to get the desired effect on the subject (as described, for example, in the '962 patent, the '454 publication, and the '957 application). A handheld controller with a communication link to the control electronics of the drive 200 may be used by the health care provider or the subject him- or herself, Readings of the speed and peak acceleration could also be available. The control electronics also incorporate a "patient stop switch" which may be given to the subject to hold. The motors would stop whenever the switch was activated.

Although this reciprocating movement platform is well designed for providing a wide range of controlled motions to a subject on it, it is fairly heavy, and, as such, may not be appropriate for usage in the more. Thus, there is a need for a reciprocating movement platform with reduced weight.

SUMMARY OF THE INVENTION

It is an object of the present invention to provide an apparatus and method of causing the external addition of pulses to the fluid channels of a subject based on the periodic acceleration of the subject's body.

It is another object of the present invention to provide a simplified apparatus which is more suitable and economical for home treatments than past devices.

It is yet another object of the present invention to provide medical treatments based on the periodic acceleration of the subject's body, where said periodic acceleration causes the external addition of pulses to the fluid channels of the subject.

The presently preferred embodiment of an apparatus of the present invention comprises a box frame, a drive module, and a support connected to the drive module. The support has a planar surface for supporting the subject, and a footboard to hold the subject's feet. The drive module provides periodic acceleration to the subject by moving in a line parallel to the planar surface of the support.

The presently preferred medical treatments possible with externally applied periodic acceleration according to the present invention include the treatment and prevention of cancer as well as diminishing the unwanted side effects of chemotherapy and radiotherapy, and the chronic preconditioning, immediate preconditioning, and/or postconditioning of subjects, such as athletes, to prevent and/or treat prevent/treat any of the insalubrious conditions which may be caused by athletic activity, whether such activity is continuous, periodic, or intermittent as well as to improve sports performance.

The presently preferred medical treatments possible with externally applied periodic acceleration according to the present invention also include chronic treatments to minimize organ damage caused by an unforeseen future stroke, coronary artery thrombosis, pulmonary embolism, etc. The presently preferred medical treatments possible with externally applied periodic acceleration according to the present invention include attenuation of left ventricular remodeling and promotion of reverse left ventricular remodeling. The presently preferred medical treatments possible with externally applied periodic acceleration according to the present invention include attenuation of the inflammatory and cognitive deficit complications of coronary artery bypass surgery, diminution of cardiac allograph vasculopathy as well as aiding angiogenesis in ischemic tissue.

The presently preferred medical treatments possible with externally applied periodic acceleration according to the present invention include the cognitive and learning deficits as well as behavioral abnormalities in early cognitive impairment, Alzheimer's disease, vascular dementias, Parkinson's disease, amyotrophic lateral sclerosis, Huntington's chorea, Wilson's disease, suprabulbar palsy and possibly Tourette syndrome. The presently preferred medical treatments possible with externally applied periodic acceleration according to the present invention includes hereditary hemorrhagic telangiectasia. The presently preferred medical treatments possible with externally applied periodic acceleration according to the present invention include migraine and prion diseases.

The presently preferred medical treatments possible with externally applied periodic acceleration according to the present invention includes the ageing process and management of Sjogren's syndrome, Lyme disease, and the Gulf War syndrome. The presently preferred medical treatments possible with externally applied periodic acceleration according to the present invention includes treatment of cystic fibrosis, chronic bronchitis, asthma, chronic sinusitis and adult and infant respiratory distress syndrome, SARS and chronic otitis media as well as the adverse effects of mechanical ventilation that cause damage to the lung. The presently preferred medical treatments possible with externally applied periodic acceleration according to the present invention includes corticosteroid resistant asthma, Crohn's disease and ulcerative colitis.

The presently preferred medical treatments possible with externally applied periodic acceleration according to the present invention include improving nail growth and nail brittleness.

The presently preferred medical treatments possible with externally applied periodic acceleration according to the present invention includes preventing and treating the serious side effects of cell free hemoglobin transfusions.

The presently preferred medical treatments possible with externally applied periodic acceleration according to the present invention includes treatment of the consequences of injuries from a nuclear explosion, "dirty bomb" or nuclear power plant attack.

The various features of novelty which characterize the invention are pointed out with particularity in the claims annexed to and forming a part of the disclosure. For a better understanding of the invention, its operating advantages, and specific objects attained by its use, reference should be had to the drawing and descriptive matter in which there are illustrated and described preferred embodiments of the invention. It is to be understood, however, that the drawings are designed solely for purposes of illustration and not as a definition of the limits of the invention, for which reference should be made to the appended claims. It should be further understood that the drawings are not necessarily drawn to scale and that, unless otherwise indicated, they are merely intended to conceptually illustrate the structures and procedures described herein.

BRIEF DESCRIPTION OF THE DRAWINGS

In the drawings:

FIGS. 3A-3E are diagrams showing the movement of a single pair of drive weights according to a previously described embodiment of the present invention;

DETAILED DESCRIPTION OF THE PRESENTLY PREFERRED EMBODIMENTS

Figure 1:
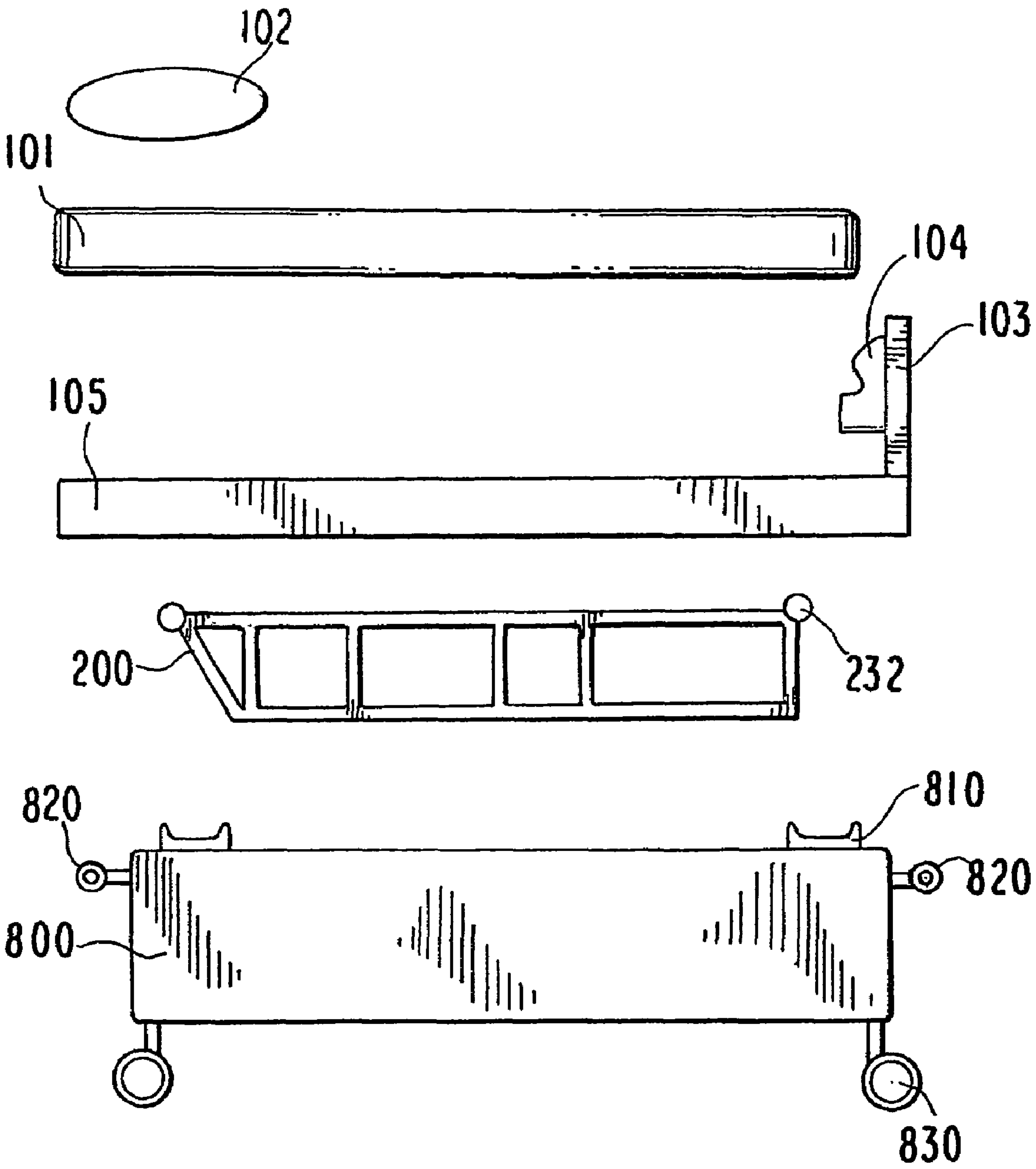
FIG. 1 is an exploded view of the components in a reciprocating movement platform according to embodiments of the present invention.
Figure 2A:
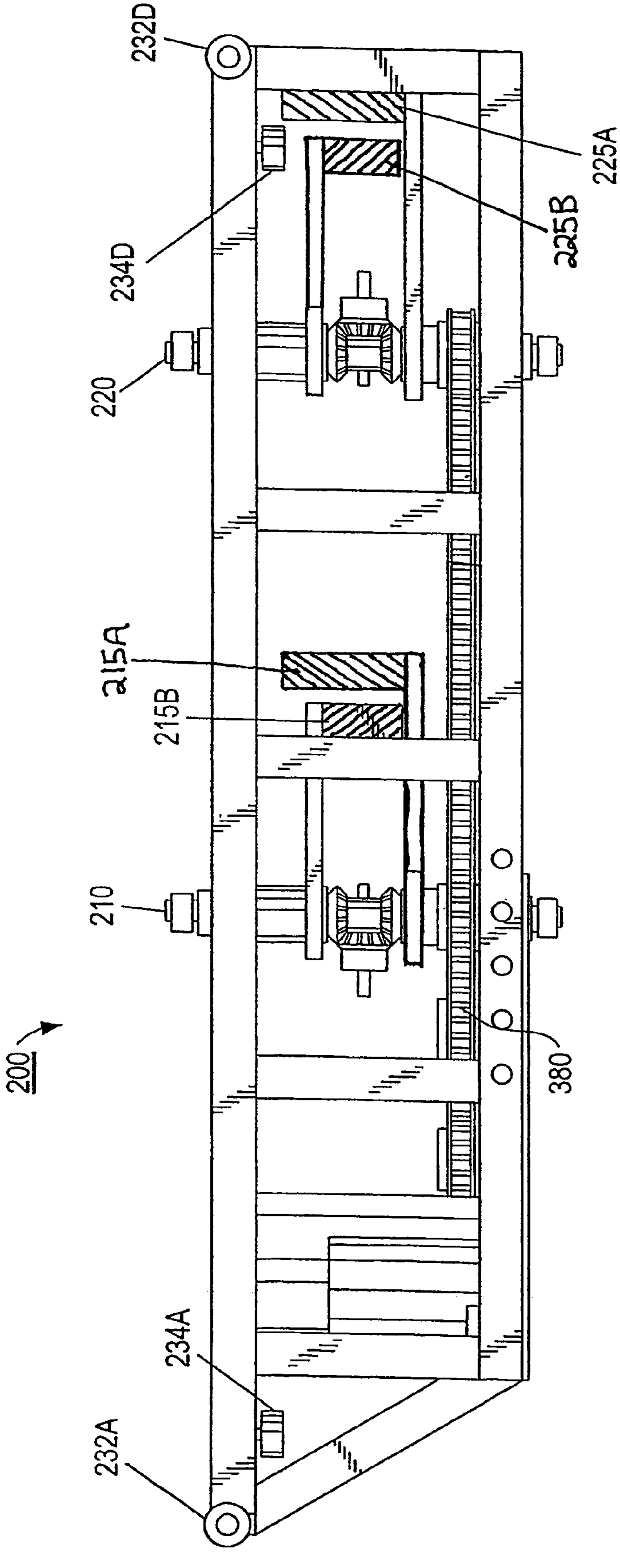
FIG. 2A is a schematic drawing of a side view of a drive according to a previously described preferred embodiment of the present invention.
Figure 2B:
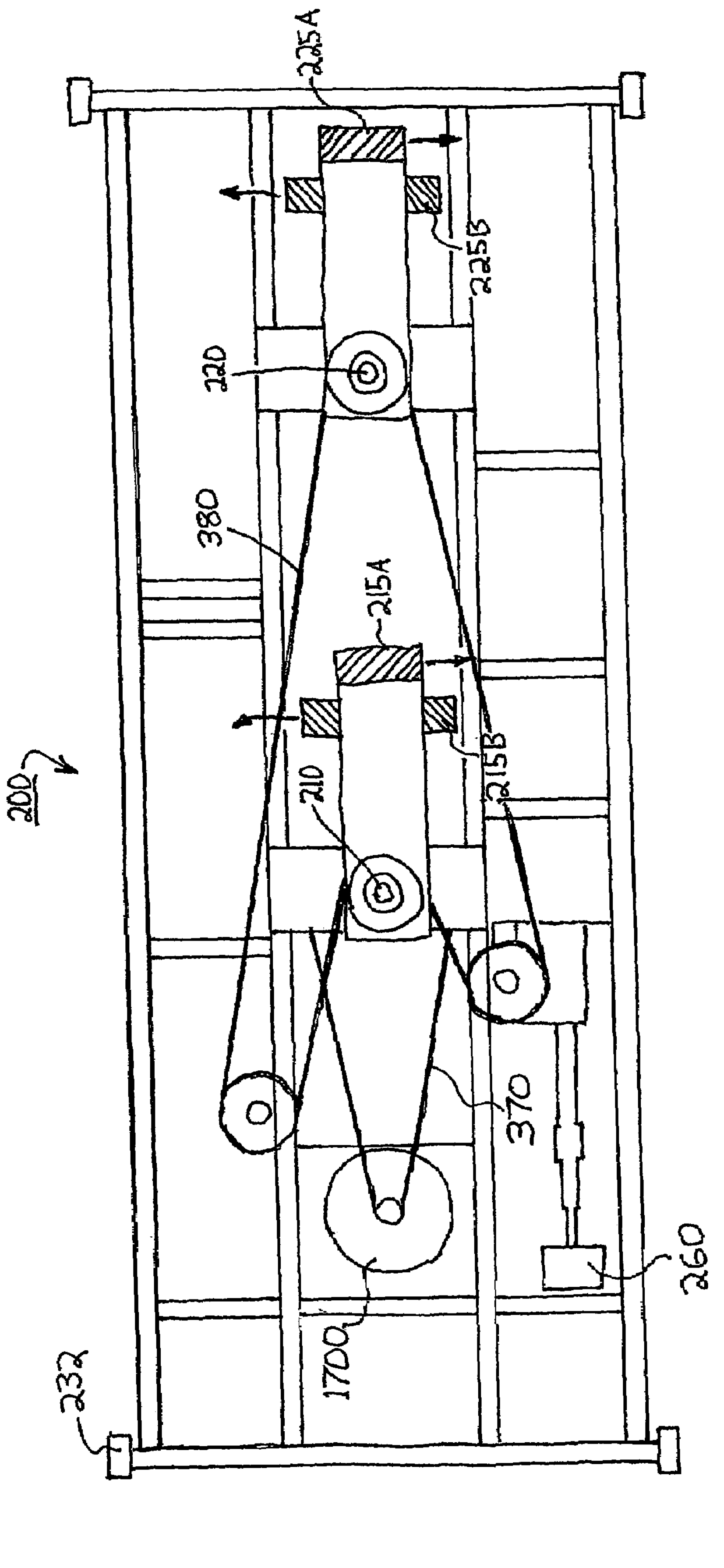
FIG. 2B is a schematic drawing of a top view of a drive according to a previously described preferred embodiment of the present invention.
Figure 4:
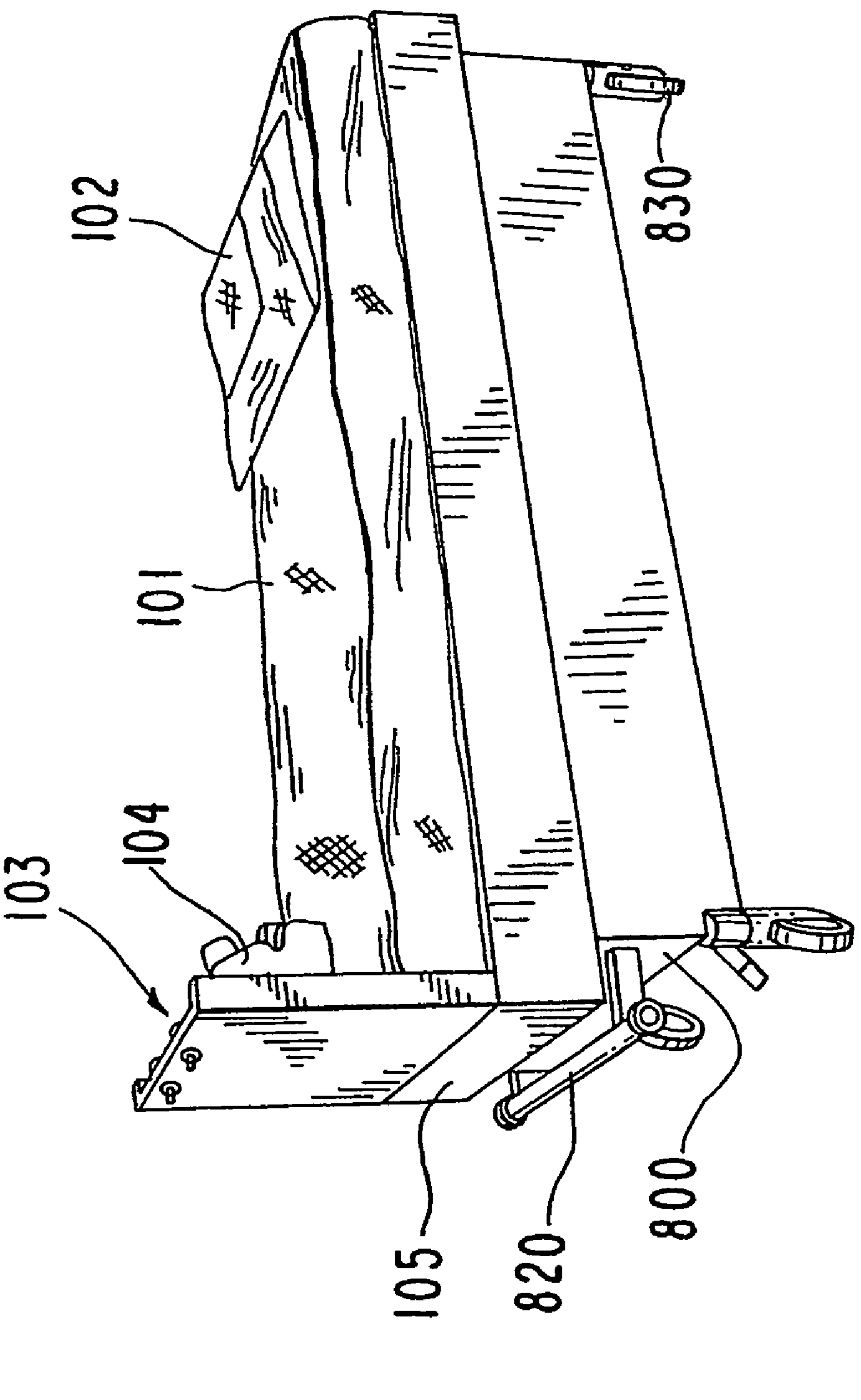
FIGS. 4, 5, and 6 are different views of a completely assembled reciprocating movement platform according to a previously described preferred embodiment of the present invention.
Figure 5:
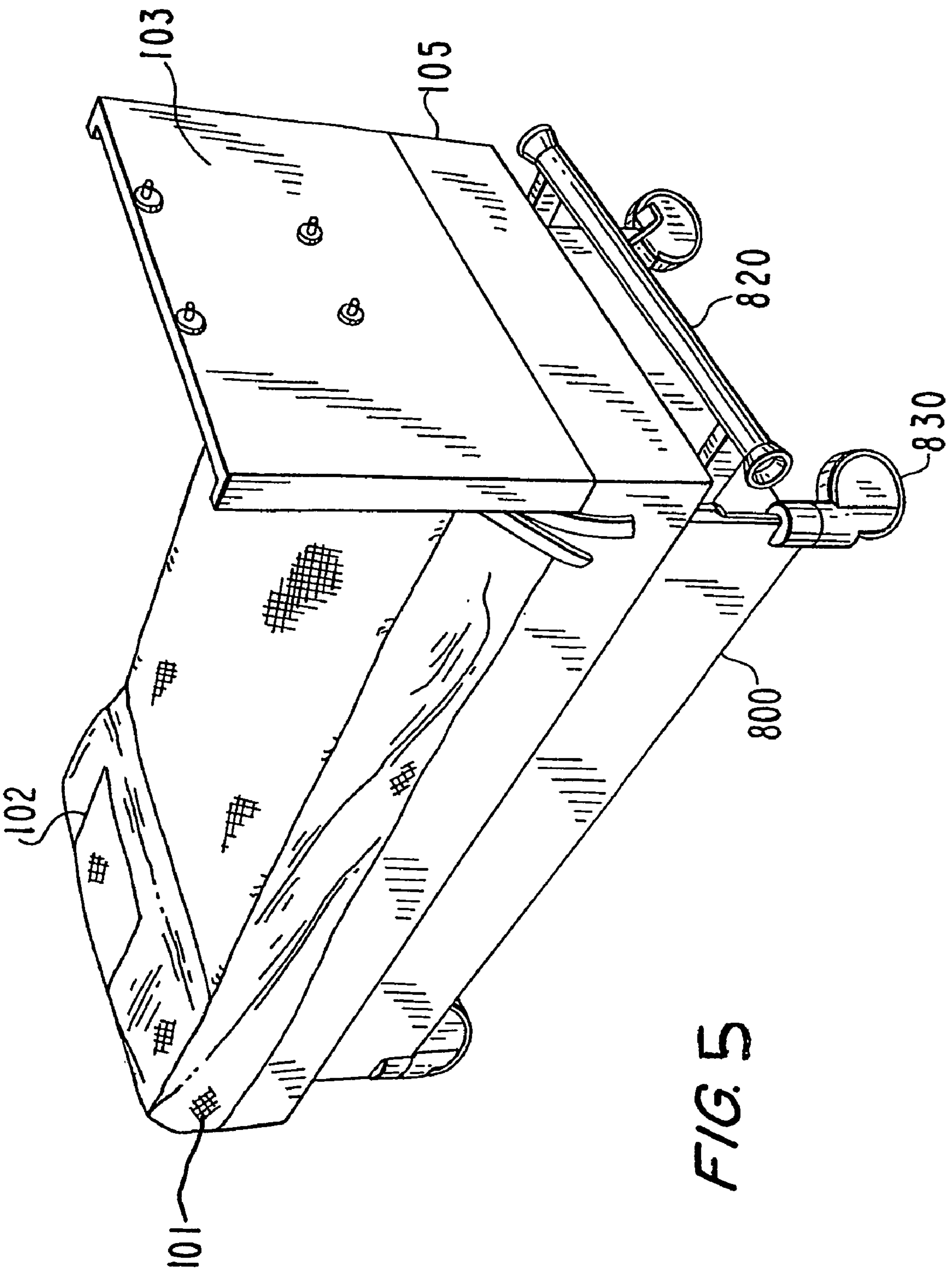
Figure 6:
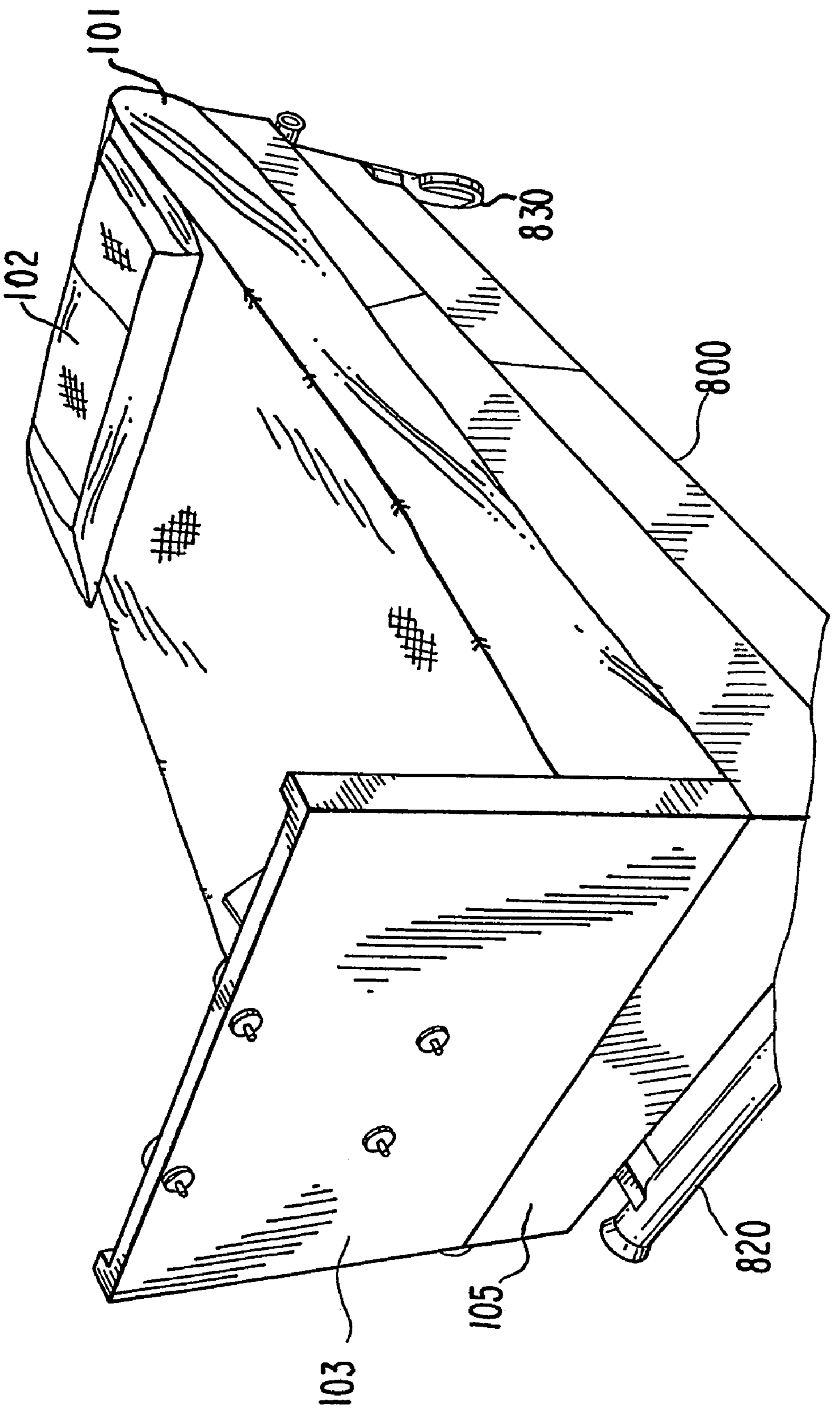
Figure 7:
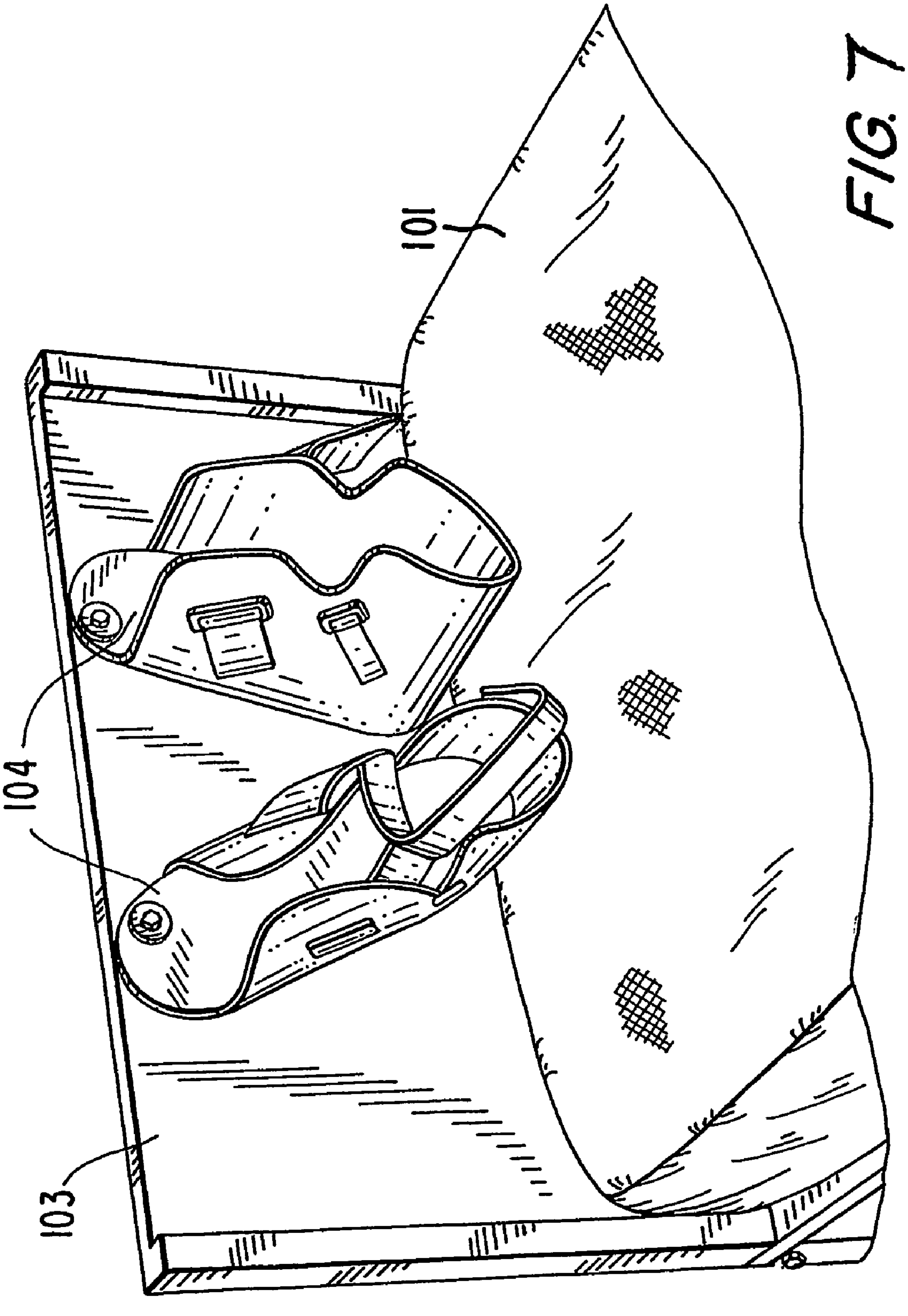
FIG. 7 shows cast shoes and a footboard support according to a previously described preferred embodiment of the present invention.

The present invention relates to both an apparatus and methods of treatment using periodic acceleration. This portion of the application is broken into two sections: section I will describe some preferred embodiments of the apparatus, and section II will describe methods of treatment.

I. The Reciprocating Movement Platform

In the current commercial model of the reciprocating movement platform, controls are available to adjust cycling speed and amplitude of platform displacement. This combination can be monitored by an accelerometer to estimate of the magnitude of applied periodic gravitational (i.e., acceleration-based) forces. This current model is capable of fine-tuning, but is also fairly heavy, and is thus appropriate for use in an institution, such as a clinic or hospital, or a doctor's office.

Using a dose response curve of nitric oxide released from periodic acceleration (obtained from analysis of the descent of the dicrotic notch of the finger pulse using a photoelectric-plethysmographic sensor), it has been determined that, with the motion platform cycling rate fixed at 140 cycles per minute, periodic acceleration values between ±0.20 and ±0.30 g produced more effective release of nitric oxide than ±0.15 or ±0.10 g. (Sackner M A, Gummels E M, Adams J A. *Dose responsiveness of dicrotic notch position in periodic acceleration*. Am. J. Respir. Crit. Care Med. 169[7], A178. 2004.). For adults with normal body weight, settings of approximately ±0.20 g and rate of 140 cycles per minute and for obese adults, settings of approximately ±0.17 and rate of 140 cycles per minute provide a proper balance between nitric oxide release and subject comfort during periodic acceleration treatments. However, to be more certain of such settings, it may be necessary to analyze the position of the dicrotic notch and the amplitude of cycling and the time of the cycle as a measure of nitric oxide release with the current periodic acceleration motion platform to more precisely set the appropriate parameters for the home model.

Thus, since periodic acceleration gravitational forces within a narrow range produce an effective release of nitric oxide, it was realized that a simplified reciprocating platform is possible, where the amount of machinery in the embodiments described in the '957 application can be sharply reduced, resulting in a reduction of the weight of the platform by hundreds of pounds, and thereby making a more suitable and economical home model reciprocating platform.

In one embodiment of the presently preferred invention, the amount of displacement of drive module 200 is fixed, rather than variable, as it is in the '957 application. With such a change, the complex machinery in the embodiments of the '957 application are no longer necessary. Specifically, there is no need for the two large, heavy electrical motors, or the complex system of fly wheel belt assemblies which provide both the speed and displacement adjustments in the '957 application.

The new "home unit" motion platform will provide variable speed, but fixed displacement. It will use the existing welded box frame 800, or a bolted, wrought aluminum modular box frame (with greatly reduced weight), such as the modular elements made by Item, Solingen, Germany. A simplified motor driving system will be attached to the box frame 800 rather than being contained within drive module 200, as it is in the '957 application. This simplified motor driving system will 'push' and 'pull' drive 200 through a sinusoidal horizontal, head to foot motion of approximately 2.5 cm or less. The stroke distance is fixed during manufacture for the desired periodic acceleration gravitational setting. The cycling speed is adjusted to a given range of speeds. The presently preferred drive for the home model device is a rotary eccentric mounted to box frame 800, but coupled to drive 200. It is powered by an adjustable AC drive motor, powered via a 120 VAC, single-phase input (50 or 60 Hz). The adjustable AC drive motor provides an adjustable frequency and voltage output of 0-60 Hz, 0-230 VAC, 3-phase power. An example of such a variable speed AC drive motor rated at ½ HP is manufactured by AC Tech (Model SM005S, AC Technology, Usbridge, Mass. 01569). It has an adjustable acceleration/deceleration control; the variable speed can be controlled thereby via a front panel.

The adjustable AC drive motor powers a three-phase induction, brushless motor from 0 to 1800 rpm with a totally enclosed, non-ventilated, flange (AG induction motor, 56C flange, TENV construction, 230VAC, 3 ph, 60 Hz, Baldor Electric Company, Fort Smith Ark. 72901) mounted to an industrial rated right angle worm reducer of 10:1 reduction that converts the rotary motion of the shaft of the AC motor into linear displacement. The worm reducer is provided with an output shaft, whereupon the rotary eccentric drive is fixed and keyed. The worm reducer with 56C face input is scaled for lift lubrication (Model NMRV-040-10:1-56 C, Motovario, Alpharetta, Ga. 30005). On the end of the worm reducer output shaft is a plate that can be securely bolted to another plate attached to the flat surface of one end of the frame of drive module 200, thereby imparting a head to foot linear sinusoidal motion. It should be recognized that other models of the components of the drive and frame and manufacturers could be substituted for these "off the shelf" parts in the fabrication of the home periodic acceleration, motion platform device. Furthermore, different constructions and architectures may be used, as would be known to one skilled in the art, for having a motor attached to box frame 800 which imparts the head to foot motion of drive module 200.

Treatments with periodic acceleration are self-limited for acute soft tissue and bone injuries. They serve as a jump-start for patients in whom aerobic exercise is one of the recommended first line treatments such as coronary artery disease, peripheral vascular disease, fibromyalgia and chronic fatigue syndrome. However, treatment is lifetime for most chronic inflammatory diseases that encompass 1) neurological diseases such as Alzheimer's disease, Parkinson's disease, multiple sclerosis, amyotrophic lateral sclerosis, neuropathy, etc., 2) rheumatological diseases such as osteoarthritis, rheumatoid arthritis, etc., 3) gastrointestinal diseases such as Crohn's disease, ulcerative colitis, etc., 4) liver diseases such as hepatitis C and portal cirrhosis, 5) kidney diseases such as glomerulonephritis, etc. 6) urinary tract diseases such as interstitial cystitis, etc. Therefore, a cheaper, simplified, periodic acceleration device of less weight than the current design is needed for home applications. Further, the external appearance may take several forms depending upon use and consumer preferences, viz., a stand alone medical device, to also serve as a single or queen size bed for sleeping, or to be incorporated into a sofa design and also serve for sitting. The dimensions of the frame can be increased in width to accommodate two individuals or side-to-side periodic acceleration.

The use of the digital pulse wave and R wave trigger recording from the electrocardiograph during varied settings of periodic acceleration amplitude and rate in cycles per minute allows analysis of the descent of the dicrotic notch as described in the '957 application. The magnitude of descent of the dicrotic notch and/or the cycle length and magnitude of the rise and fall of the dicrotic notch during periodic acceleration provides an estimate of the effectiveness of nitric oxide released from activation of endothelial nitric oxide synthase by pulsatile shear stress. This enables transfer of optimal settings from the current device to the home device that allows control of rate with a fixed setting for amplitude adjusted in the factory where the home device is manufactured.

II. Methods of Treatment

This section will describe preferred embodiments of medical treatments using a reciprocating movement platform. Although use of the preferred embodiment of the reciprocating movement platform is preferred and the descriptions below are based on its use, another type of device which could apply pulses in the manner appropriate for the particular treatment (as discussed below) may be used.

In addition to the treatments previously disclosed in the '976 patent, the '454 publication, and the '957 application, periodic acceleration according to the present invention may be used to

- A) treat and/or prevent cancer, as well as provide relieve to the unwanted side effects of cancer treatment,
- B) serve as a means of preconditioning or conditioning,
- C) manage obesity and weight control generally;
- D) promote ventricular remodeling;
- E) treat and/or prevent atrial fibrillation;
- F) managing complications of coronary artery bypass surgery;
- G) treat and/or prevent cognitive and learning deficits, behavioral abnormalities, and/or diseases which affect the cognitive function;
- H) treat and/or prevent atherosclerosis;
- I) promote angiogenesis in ischemic tissues;
- J) treat and/or prevent talangiectasia;
- K) treat and/or prevent migraines;
- L) treat and/or prevent prion diseases;
- M) manage the aging process;
- N) manage Sjogren's Syndrome;
- O) manage Lyme Disease;
- P) manage Gulf War Syndrome;
- Q) manage miscellaneous pulmonary effects;
- R) treat corticosteroid resistance;
- S) treat chronic otitis media;
- T) promote nail growth and strength;
- U) manage the side effects of cell free hemoglobin transfusions; and
- V) treat radiation injuries.

A. Treatment of Cancer

Tumors in which nuclear factor kappa beta is present in the nucleus of cells (constitutive activation) include the following among others (Garg A, Agawam B. *Nuclear transcription factor-kappa B as a target for cancer drug development*. Leukemia 2002; 16:1053-68); Bus-Ramos C E, Roche F C, Shishodia S, Medeiros L J, Kantarjian H M, Vadhan-Raj S, Estrov Z, Smith T L, Nguyen M H Aggarwal B B. *Expression of constitutively active nuclear-kappa B RelA transcription factor in blasts of acute myeloid leukemia*. Hum Pathol 2004; 35: 246-253):

B cell lymphoma
Hodgkin's disease
T cell lymphoma
adult T cell lymphoma
acute lymphoblastic leukemia
mantle cell lymphoma
myeloid leukemias
gastric cancer
breast cancer
liver cancer
thyroid cancer
cervical cancer
pancreatic cancer
prostate cancer
mesothelioma
melanoma
head and neck squamous cell carcinoma
colorectal cancer
multiple myeloma
ovarian cancer
bladder cancer
lung cancer
vulvar cancer
brain tumors
fibrosarcoma
osteosarcoma
neuroblastoma Tumorigenesis is characterized by self-sufficiency in growth signals, insensitivity to growth inhibition, evasion of apoptosis, immortalization, sustained angiogenesis, tissue invasion and metastasis. (Hanahan D, Weinberg R A. *The hallmarks of cancer*, Cell. 2000;100:57-70). Nuclear factor kappa beta that is constitutively activated in tumor cells promotes tumorigenesis since this gene produces negative feedback of nuclear factor kappa beta, causes cancer cell proliferation, prevents apoptosis (programmed cell death), increases angiogenesis, and increases metastatic potential. (Garg A, Aggarwal B B. *Nuclear transcription factor-kappa B as a target for cancer drug development*. Leukemia 2002: 16:1053-68; Bharti A C, Aggarwal B B. *Nuclear factor-kappa B and cancer: its role in prevention and therapy*. Biochem. Pharmacol 2002; 64:883-88). Because of these factors, Karin suggested that nuclear factor kappa beta should receive as much attention from cancer researchers as it has already from immunologists (Karin M, Cao Y, Greten F R, Li Z W. *NF-kappaB in cancer: from innocent bystander to major culprit*, Nat. Rev. Cance. 2002; 2:301-10).

Indeed, pharmacological agents that block nuclear factor kappa beta activity have been employed to treat cancerous cell lines with success (Fujioka S, Sclabas G M, Schmidt C, Niu J, Frederick W A, Dong Q G et al. *Inhibition of constitutive NF-kappa B activity by I kappa B alpha M suppresses tumorigenesis*, Oncogene 2003; 22:1365-70; Liptay S, Weber C K, Ludwig L, Wagner M, Adler G, Schmid R M. *Mitogenic and antiapoptotic role of constitutive NF-kappaB/Rel activity in pancreatic cancer*. Int. J. Cancer 2003; 735-46; Umezawa K, Ariga A, Matsumoto N. *Naturally occurring and synthetic inhibitors of NF-kappaB functions*, Anticancer Drug Des 2003; 15:239-44).

Although activation of nuclear factor kappa beta in cancer cells plays a major role in tumorigenesis, other factors as well contribute including overexpression of 1) vascular endothelial growth factor (VEGF), 2) interleukin 8 (IL-8), 3) large quantities of nitric oxide from inducible nitric oxide synthase (iNOS) activity, 4) mutated p53, 5) epidermal growth factor receptor (EGFR), 6) tumor necrosis factor superfamily, and 7) COX2. Vascular endothelial growth factor (VEGF) and interleukin-8 (IL-8) expressed by tumors promote angiogenesis thereby providing a blood supply to fuel tumor growth. VEGF induces proliferation of endothelial cells, increases vascular permeability, and induces activation of plasminogen activators by such cells, VEGF and IL-8 are directly expressed by tumor cells and also stimulated by nuclear factor kappa beta activation. (Xiong H Q, Abbruzzese J L, Lin E et al. *NF-kappaB activity blockade impairs the angiogenic potential of human pancreatic cancer cells*. Int J Cancer 2004; 108(2): 181-188; Huang S, Robinson J B, Deguzman A et al. *Blockade of nuclear factor-kappaB signaling inhibits angiogenesis and tumorigenicity of human ovarian cancer cells by suppressing expression of vascular endothelial growth factor and interleukin* 8. Cancer Res 2000; 60(19):5334-5339).

Large quantities of nitric oxide expressed through activation of iNOS in cancer cells facilitate tumor progression. Nitric oxide produced from iNOS in at a low level in ulcerative colitis and sporadic colorectal cancer activates p53, which is anti-tumorigenic, but at a high level of production, NO may cause mutations in p53 thereby acting in a pro-tumorigenic role. Under normal circumstances, the tumor suppressor p53 is a sensor of diverse cellular stresses including DNA damage, oxidative stress, and hypoxia, and aids in directing cell cycle arrest and apoptosis (physiological programmed death of cells) through transcriptional activation of target genes like p21. p53 is the most commonly mutated gene in a broad spectrum of cancers and is often associated with tumor progression, resistance to therapy, and poor prognosis. In melanoma, p53 rarely mutates but increased expression associated with tumor progression correlates well with iNOS activity. Increased nitric oxide from activation of iNOS in melanoma cells also correlates with resistance to chemotherapeutic agents. (Goodman J E, Hofseth L J, Hussain S P et al. *Nitric oxide and p53 in cancer-prone chronic inflammation and oxyradical overload disease*. Environ Mol Mutagen 2004; 44(1):3-9; Tang C H, Grimm E A. *Depletion of endogenous nitric oxide enhances cisplatin-induced apoptosis in a p53-dependent manner in melanoma cell lines*. J Biol Chem 2004; 279(1):288-298.)

Epidermal growth factor receptor (EGFR) is overexpressed in tumors such as lung, colon, kidney, prostate, breast, and head and neck carcinomas, which are mostly resistant to current chemotherapies. EGF prevents apoptosis or programmed death of cancer cells like nuclear factor kappa beta, thereby rendering them immortal. Activation of the EGFR-TK enzyme also results in autophosphorylation, which drives signal transduction pathways leading to tumor growth and malignant progression. When EGFR activation is blocked with anti EGFR drugs, VGFR and IL-8 production falls. However, use of anti-EGFR agents may be associated with the side effects of skin rash and diarrhea and less frequently interstitial pneumonitis. The EGFR-TK inhibitor gefitinib (Iressa) shows clinical benefits in patients with advanced non-small cell lung cancer whose disease had previously progressed on platinum- and docetaxel-based chemotherapy regimens. (Lage A, Crombet T, Gonzalez G. *Targeting epidermal growth factor receptor signaling: early results and future trends in oncology*. Ann Med 2003; 35(5):327-336; Vlahovic G, Crawford J. *Activation of tyrosine kinases in cancer*. Oncologist 2003; 8(6):531-538.)

The tumor necrosis factor (TNF) superfamily of inflammatory cytokines mediates either proliferation, survival, or apoptosis of cells. Although distinct receptors, all members share a common cell signaling pathway that mediates the activation of nuclear factor-kappaB (NF-kappaB) and mitogen-activated protein kinases (e.g. c-jun N-terminal kinase). Under specific conditions TNF alpha is a tumor promoter and helps to produce the toxic effects associated with conventional cancer therapy, such as the cytokine release syndrome and cisplatin-induced nephrotoxicity. (Gaur U, Aggarwal B B. *Regulation of proliferation, survival and apoptosis by members of the TNF superfamily*. Biochem Pharmacol 2003; 66(8):1403-1408; Szlosarek P W, Balkwill F R. *Tumour necrosis factor alpha: a potential target for the therapy of solid tumours*. Lancet Oncol 2003; 4(9):565-573.)

Cyclooxygenase 2 (COX2) overexpression that is found most commonly in lung and colorectal cancers contributes to the tumorigenesis by at least five different mechanisms including transformation of procarcinogens on carcinogens, pro-inflammatory and immunomodulatory effect, resistance to apoptosis, angiogenesis and invasion progression. Therefore, treatment with a COX2 inhibitor in such tumors retards tumor progression. (Gasparini G, Longo R, Sarmiento R et al. *Inhibitors of cyclo-oxygenase 2: a new class of anticancer agents?* Lancet Oncol 2003; 4(10):605-615).

Adhesion of circulating tumor cells to microvascular endothelium plays an important role in tumor metastasis. Tumor cells are more likely to adhere to postcapillary venules than to corresponding precapillary arterioles thereby playing an important role in tumor metastasis to distant organs. (Kong L, Dunn G D, Keefer L K et al. *Nitric oxide reduces tumor cell adhesion to isolated rat postcapillary venules*. Clin Exp Metastasis 1996; 14(4):335-3).

A major problem in human cancers is to distribute the pharmacological agent to the tumor without producing toxicity to normal cells. Nitric oxide released from eNOS with periodic acceleration offers a non-toxic means to suppress activated nuclear factor kappa beta (Stefano G B, Prevot V, Cadet P, Dardik I. *Vascular pulsations stimulating nitric oxide release during cyclic exercise may benefit health: a molecular approach* (*review*), Int. J. Mol. Med. 2001; 7:119-29). Further, since tumors are characterized by a well-developed blood supply, distribution of the nitric oxide suppressant activity on activated nuclear factor kappa beta does not pose a problem. Both aerobic exercise and periodic acceleration increase shear stress to the endothelium but there are differences between the two with respect to distribution of blood flow and NO from eNOS, particularly with regard to the viscera. Aerobic exercise causes diminution of blood flow to the internal organs whereas periodic acceleration increases blood flow to these organs, e.g., liver, gastrointestinal tract, and kidneys. (Adams J A, Mangino M J, Bassuk J et al. *Regional blood flow during periodic acceleration*. Crit Care Med 2001; 29(10):1983-1988.). Miyauchi et al. showed that both eNOS activity and NOx are diminished in the kidneys along with decreased blood flow with exercise while the opposite takes place with pulmonary blood flow. (Miyauchi T, Maeda S, Lemitsu M et al. *Exercise causes a tissue-specific change of NO production in the kidney and lung*. J Appl Physiol 2003; 94(1):60-68.)

Periodic acceleration through nitric oxide release from activation of eNOS suppresses activity of nuclear factor kappa beta. This was recently demonstrated in a sheep model of asthma, which is an example of an nuclear factor kappa beta disease. Periodic acceleration (pGz) stimulates NO release from endothelial nitric oxide synthase (eNOS) through pulsatile shear stress (Adams et al. *Effects of periodic body acceleration on the in vivo vasoactive response to N-w-nitro-L-arginine and the in vitro nitric oxide production*. Ann. Biomed. Engineer. 2003;31:1337). It was found that: a) pretreatment with pGz significantly blunts the early (EAR) probably through NO preventing mast cell degranulation and blocks the late (LAR) allergen-induced airway responses in allergic sheep; b) pGz-induced protection is lost if the eNOS inhibitor, L-NAME, is given 30 min before pGz treatment and c) initiating pGz 2h after antigen challenge still blocks the LAR (Abraham et al. *Periodic acceleration via nitric oxide modifies antigen-induced airway responses in sheep*. Am. J. Respir. Crit Care Med. 2004;169:A321). NF-kB is a transcription factor for inflammatory cytokines involved in the LAR. There are reports that eNOS generated NO suppresses NF-kB activity (Blues'., Rivet's. *Inhibitory action of nitric oxide on circulating tumor necrosis factor-induced NF-kappaB activity and COX-2 transcription in the endothelium of the brain capillaries*. Neuropathol. Exp. Neurol. 2001;60: 893). To determine if pGz suppresses NF-kB activity thereby affecting antigen-induced airway responses, we performed bronchoalveolar lavage 6h after antigen challenge and measured free p65 levels in lavage cell nuclear extracts (an indicator of NF-kB activation) by ELISA. Peak LAR (% increase over baseline) in control, pGz-treated and L-NAME+pGz treated sheep (all n=6) were 118±2%, 21±4% and 130±4%, respectively. Levels of p65/$10^6$ cells were 1.9- and 1.8-fold higher in the control and L-NAME+pGz groups (both $p<0.05$) when compared to pGz treated animals. Therefore, pGz stimulates eNOS and increases NO throughout the body, which can block NF-kB-mediated inflammation. (Sackner, M. A., Laredo, I. T., Serebriakov, I., Adams, J. A., Bassuk, J., Abraham, W. M. *Periodic acceleration modifies antigen-induced airway responses in sheep by nitric oxide (NO)-mediated down regulation of nuclear factor kappa beta (NF-kB)*. Eur. Resp. J. 2004; 24: in press).

Nitric oxide released from eNOS with periodic acceleration acts on other tumorigenic mediators directly or indirectly through nuclear factor kappa beta. Nuclear factor kappa beta regulates the expression of vascular endothelial growth factor (VEGF) and IL-8, The decreased expression of VEGF and interleukin 8 directly correlate with decreased tumorigenicity, decreased vascularization of lesions, decreased formation of malignant ascites, and prolonged survival in several cancers, e.g., pancreatic, ovarian, etc. (Xiong H Q, Abbruzzese J L, Lin E et al. *NF-kappaB activity blockade impairs the angiogenic potential of human pancreatic cancer cells*. Int J Cancer 2004; 108(2):181-188; Gilmore T, Gapuzan M E, Kalaitzidis D et al. *Rel/NF-kappa B/I kappa B signal transduction in the generation and treatment of human cancer*. Cancer Lett 2002; 181(1):1-9.) Thus, suppression of nuclear factor kappa beta activity with NO released from eNOS with pGz indirectly suppresses tumorigenesis by downregulating VEGF and IL-8. Although its action on nuclear factor kappa beta activity is favorable as anti-tumorigenic, NO released from eNOS by periodic acceleration might be considered potentially harmful because under certain circumstances it stimulates VEGF that might help tumor spread by angiogenesis. However, there are conflicting data of NO effects on VEGF that relate to the amount of released NO which can be a positive or negative modulator of the VEGF gene under the same conditions. The VEGF-mediated angiogenesis requires NO production from activated endothelial NO synthase (eNOS). Activation of eNOS by VEGF involves several pathways including Akt/PKB, Ca(2+)/calmodulin, and protein kinase C. The NO-mediated VEGF expression can be regulated by HIF-1 and heme oxygenase 1 (HO-1) activity, and the VEGF-mediated NO production by eNOS can be also modulated by HIF-1 and HO-1 activity, depending upon the amount of produced NO. These reciprocal relations between NO and VEGF may contribute to regulated angiogenesis in normal tissues. (Kimura H, Esumi H. Reciprocal regulation between nitric oxide and vascular endothelial growth factor in angiogenesis. Acta Biochim Pol 2003; 50(1):49-59.) In 10 normal subjects who received 35 daily periodic acceleration treatments, plasma VEGF doubled from baseline measurements at the end of seven weeks but was still within the upper range of normal values and similar to the VEGF elevation experienced by endurance athletes after acute exercise. (Kraus R M, Stallings H W, III, Yeager R C et al. Circulating plasma VEGF response to exercise in sedentary and endurance-trained men. J Appl Physiol 2004; 96(4):1445-1450.) In metastatic cancers, plasma VEGF greatly exceeds normal values of VEGF, for example with metastatic lung cancers, it may be 10 times the normal value. (Kishiro I, Kato S, Fuse D et al. Clinical significance of vascular endothelial growth factor in patients with primary lung cancer. Respirology 2002; 7(2):93-98.) Thus, the periodic acceleration VEGF suppressant effect through inhibition of nuclear factor kappa beta activity is of greater importance in anti-tumorigenesis than the pro-tumorigenesis effect of VEGF in angiogenesis.

Periodic acceleration by releasing small quantities of NO from eNOS suppresses iNOS activity, which is usually pro-tumorigenic. It also scavenges reactive oxygen species (ROS) and reactive nitrogen species (RNS) that are pro-tumorigenic (Stefano G B, Goumon Y, Bilfinger T V et al. *Basal nitric oxide limits immune, nervous and cardiovascular excitation: human endothelia express a mu opiate receptor*. Prog Neurobiol 2000; 60(6):513-530). This action of periodic acceleration therefore may help to prevent and treat colorectal and other cancers. (Hussain S P, Amstad P, Raja K et al. *Increased p53 mutation load in noncancerous colon tissue from ulcerative colitis: a cancer-prone chronic inflammatory disease*. Cancer Res 2000; 60(13):3333-3337. The tumor suppressor p53 is a sensor of diverse cellular stresses including DNA damage, oxidative stress, and hypoxia, and helps to direct cell cycle arrest and apoptosis through transcriptional activation of target genes like p21. p53 is the most commonly mutated gene in a broad spectrum of cancers and is frequently associated with tumor progression, resistance to therapy, and poor prognosis. In melanoma, p53 rarely mutates but increased expression associated with tumor progression and correlates well with iNOS activity. The reason for paradoxical activity of p53 thought to be some sort of dysregulation problem. Therefore, suppression of iNOS activity by eNOS activated with periodic acceleration promotes the normal tumor suppressor function of p53. (Tang C H, Grimm E A. *Depletion of endogenous nitric oxide enhances cisplatin-induced apoptosis in a p53dependent manner in melanoma cell lines*. J Biol Chem 2004; 279(1):288-298; Stefano G B, Goumon Y, Bilfinger T V et al. *Basal nitic oxide limits immune, nervous and cardiovascular excitation: human endothelia express a mu opiate receptor*. Prog Neurobiol 2000; 60(6):513-530.)

Nitric oxide from NO donor drugs transiently and reversibly inhibits epidermal growth factor receptors (EGFR) in neuroblastoma cells. (Murillo-Carretero M, Ruano M J, Matarredona E R et al. *Antiproliferative effect of nitric oxide on epidermal growth factor-responsive human neuroblastoma cells*. J Neurochem 2002; 83(1):119-131.). There is overexpression of epidermal growth factor receptor (EGFR) in tumors such as lung, colon, kidney breast, prostate, and, head and neck carcinomas, which are mostly resistant to current chemotherapy. Activation of the EGFR-TK enzyme results in autophosphorylation, which drives signal transduction pathways leading to tumor growth and malignant progression. EGF prevents apoptosis of cancer cells prevents apoptosis thereby immortalizing tumor cells. When EGFR activation is blocked with drugs, VGFR and IL-8 production also contribute to tumor regression. (Lage A, Crombet T, Gonzalez G. *Targeting epidermal growth factor receptor signaling: early results and future trends in oncology*. Ann Med 2003; 35(5):327-336; Vlahovic G, Crawford J. *Activation of tyrosine kinases in cancer*. Oncologist 2003; 8(6):531-538.) Repeated periodic acceleration treatments by releasing NO from nitric oxide would decrease EGFR thereby causing regression of tumor growth.

Nitric oxide from eNOS activation with periodic acceleration suppresses tumor necrosis factor superfamily indirectly through inhibition of nuclear factor kappa beta. (Zhou Z, Wang L, Song Z et al. *Abrogation of nuclear factor-kappaB activation is involved in zinc inhibition of lipopolysaccharide-induced tumor necrosis factor-alpha production and liver injury*. Am J Pathol 2004; 164(5):1547-1556.). Periodic acceleration through shear stress suppresses tumor necrosis factor alpha activity independently of activation of eNOS. (Chiu J J, Lee P L, Lee C I et al. *Shear stress attenuates tumor necrosis factor-alpha-induced monocyte chemotactic protein-*1 *expressions in endothelial cells*. Chin J Physiol 2002; 45(4):169-176.). Nitric oxide from eNOS activation with periodic acceleration scavenges COX1 and COX2 and also inhibits lipoxygenase. (Stefano G B, Magazine H I. *Nitric Oxide Autoregulation* and Its Significance. In: Stefano G B, editor, Biomedical Significance of Nitric Oxide. Warsaw-New York: Medical Science International Co., Ltd., 2003: 57-68.). Finally, NO from eNOS reduces tumor cell adhesion to blood vessels and also suppresses adhesion molecules thereby suppressing tumor metastases. (Kong L, Dunn G D, Keefer L K et al. *Nitric oxide reduces tumor cell adhesion to isolated rat postcapillary venules*. Clin Exp Metastasis 1996; 14(4):335-343; Stefano G B, Goumon Y, Bilfinger T V et al. *Basal nitric oxide limits immune, nervous and cardiovascular excitation: human endothelia express a mu opiate receptor*. Prog Neurobiol 2000; 60(6):513-530.)

The availability of nitric oxide released by activation of eNOS with periodic acceleration may be improved by vitamin and dietary supplements thereby enhancing its effects in cancer treatment as well as treatment of any condition that requires increased levels of nitric oxide from eNOS. This may be of importance where endothelial function is compromised such as in arteriosclerosis. Thus, L-ascorbic acid (vitamin C), increases nitric oxide synthase (NOS) enzyme activity via chemical stabilization of tetrahydrobiopterin (BH4). Vitamin C also increases tetrahydrobiopterin and NOS activity in blood vessels. The beneficial effect of vitamin C on vascular endothelial function appears to be mediated in part by protection of tetrahydrobiopterin and restoration of eNOS enzymatic activity. Prolonged high activity of iNOS may be detrimental to vascular function due to "uncoupling" of eNOS and subsequent formation of reactive oxygen species (ROS). (d'Uscio L V, Milstien S, Richardson D et al. *Long-term vitamin C treatment increases vascular tetrahydrobiopterin levels and nitric oxide synthase activity*. Circ Res 2003; 92(1):88-95.) An oral glucose challenge causes transient impairment of endothelial function, probably because of increased oxidative stress. During oxidative stress, endothelial nitric oxide (NO) synthase (eNOS) becomes uncoupled because of decreased bioavailability of tetrahydrobiopterin (BH4), an essential cofactor of eNOS. Administration of BH4, which is available commercially in some countries but not the United States, reverses downregulation of eNOS. (Ihlemann N, Rask-Madsen C, Perner A et al. *Tetrahydrobiopterin restores endothelial dysfunction induced by an oral glucose challenge in healthy subjects*. Am J Physiol Heart Circ Physiol 2003; 285(2):H875-H882.) Also, folic acid administration exerts direct anti-oxidative effects and contributes to restoration of impaired NO metabolism. Folate also reduces plasma homocysteine levels, enhances eNOS, and has anti-inflammatory actions. It stimulates endogenous BH4 regeneration, a cofactor necessary for NO synthesis from eNOS, inhibits intracellular superoxide generation, and thus enhances the half-life of NO. BH4 in turn enhances NO generation and augments arginine transport into the cells. Folic acid increases the concentration of omega-3 PUFAs, which also upregulates eNOS synthesis. Vitamin C augments NO synthesis from eNOS by increasing intracellular BH4 and stabilization of BH4. (Stanger O, Weger M. *Interactions of homocysteine, nitric oxide, folate and radicals in the progressively damaged endothelium*. Clin Chem Lab Med 2003; 41(11):1444-1454; Das U N. Folic acid says NO to vascular diseases. Nutrition 2003; 19(7-8):686-692.). In addition, there appears to be a benefit of higher folic acid consumption in reducing risks of colon and breast cancers. (Willett W C. *Diet and cancer*. Oncologist 2000; 5(5):393-404) Niacin in much higher doses than recommended for daily requirements elevates high density lipoprotein (HDL) and improves endothelial function by upregulating eNOS. The dose of niacin (Niaspan, KOS) is initiated at 375 mg at night and titrated to a maximal tolerated dose of 1500 mg. Patients take aspirin 30 minutes prior to niacin to minimize side effects. (Kuvin J T, Ramet M E, Patel A R et al. *A novel mechanism for the beneficial vascular effects of high-density lipoprotein cholesterol: enhanced vasorelaxation and increased endothelial nitric oxide synthase expression*. Am Heart J 2002; 144(1): 165-172.)

Das (Das U N. *Folic acid says NO to vascular diseases*. Nutrition 2003; 19(7-8):686-692) recommends the following for supplementation as an aid to achieve good endothelial function: folic acid 1 to 5 mg/day, vitamin B12 1000 ug/day, vitamin B6 5 to 10 mg/day, vitamin C 100 mg/day, L-arginine 500 mg twice a day, BH4 1 to 2 mg/Kg body weight (available in some countries but not the United States), polyunsaturated fatty acids (PUFAs) (especially eicosapentaenoic acid 120 mg/day & docosahexaenoic acid 180 mg/day. Such a supplement plan may be used in conjunction with periodic acceleration to enhance its effects on eNOS. However, Das' recommendation for the dose of L-Arginine is probably an underestimate. Oral supplementation with large amounts (6-21 g/day) of L-arginine, the precursor of endothelial-derived nitric oxide, improves endothelium-mediated vasodilation in hypercholesterolemia. Flow mediated vasodilation is improved with 6.6 g of L-Arginine administered for in the form of a nutrient bar. (Maxwell A J, Anderson B, Zapien M P et al. *Endothelial dysfunction in hypercholesterolemia is reversed by a nutritional product designed to enhance nitric oxide activity*. Cardiovasc Drugs Ther 2000; 14(3):309-316.) Lower doses are ineffective. High dosage niacin may be administered in the presence of endothelial dysfunction to produce further upregulation of eNOS.

Several chemopreventive phytochemicals have been shown to inhibit COX-2 and iNOS expression by blocking NF-kappa B activation. Curcumin, a yellow pigment of turmeric (*Curcuma longa* L., Zingiberaceae), the green tea polyphenol epigallocatechin gallate (EGCG), and resveratrol from grapes (*Vitis vinifera*, Vitaceae) strongly suppress tumor promotion because they suppress nuclear factor kappa beta. (Surh Y J, Chun K S, Cha H H et al. *Molecular mechanisms underlying chemopreventive activities of anti-inflammatory phytochemicals: down-regulation of COX-2 and iNOS through suppression of NF-kappa B activation*. Mutat Res 2001; 480-481:243-268.) These phytochemicals could potentiate the effect of periodic acceleration.

Both the immediate and late complications of radiation and/or chemotherapy may be ameliorated by periodic acceleration as pre-treatment, during treatment and post-treatment. Because radiation-induced vascular injury precedes the tissue damage, vascular injury is regarded as crucial in the pathogenesis of tissue damage. Radiation injury is marked by activation of adhesion molecules that promote leukocyte infiltration of normal tissue. Radiation activates nuclear factor kappa beta, which in turn activates adhesion molecules. (Quarmby, S.; Kumar, P.; Kumar, S. *Radiation-induced normal tissue injury: role of adhesion molecules in leukocyte-endothelial cell interactions*. Int. J. Cancer 1999;82_385-395.) Radiotherapy and chemotherapy produce numerous adverse early and late complications. Oral and gastrointestinal (GI) mucositis, a frequent complication of anticancer treatment, threatens the effectiveness of therapy because it leads to dose reductions, increases healthcare costs, and impairs patients' quality of life. (Sonis S T, Elting L S, Keefe D et al. *Perspectives on cancer therapy-induced mucosal injury: pathogenesis, measurement, epidemiology, and consequences for patients*. Cancer 2004; 100(9 Suppl):1995-2025.)

Thus, periodic acceleration alone or in conjunction with chemotherapeutic or x-ray or other cancer suppressing agents or technology offers a way to treat cancers. It may permit lesser doses of radiation and/or chemotherapy thereby minimizing deleterious side effects. Furthermore, application of periodic acceleration either alone or with other preventative agents can be used to prevent cancers. Treatment with periodic acceleration avoids the late effects of radiotherapy and chemotherapy on normal tissues. The late onset of necrosis and fibrosis in normal tissues can be a serious consequence of radiotherapy and chemotherapy in cancer patients. Because radiation-induced vascular injury precedes the tissue damage, vascular injury is regarded as crucial in the pathogenesis of tissue damage. Radiation injury is marked by activation of adhesion molecules that promote leukocyte infiltration of normal tissue. The stress of radiation or chemotherapy activated nuclear factor kappa beta in turn activates adhesion molecules. (Sonis S T, Elting L S, Keefe D et al. *Perspectives on cancer therapy-induced mucosal injury: pathogenesis, measurement, epidemiology, and consequences for patients*. Cancer 2004; 100(9 Suppl):1995-2025) Radiotherapy for abdominal and pelvic malignancies results in an increased risk of radiation enteritis. (Bismar M M, Sinicrope F A. Radiation enteritis. Curr Gastroenterol Rep 2002; 4(5):361-365.) Late effects of radiotherapy depend upon site that of radiation and may cause the following: 1) cranial radiotherapy—neurocognitive deficits, obesity, seizures and strokes, cataracts, etc. 2) chest or mantle radiotherapy—breast cancer, thyroid cancer, hypothyroidism, pulmonary fibrosis, lung cancer, cardiac fibrosis, pericarditis, etc, 3) abdominal/pelvic radiotherapy—chronic enteritis, gastrointestinal malignancy, renal failure, hemorrhagic cystitis, bladder cancer, ovarian failure, testicular failure, etc., 4) any radiation—skin cancer, melanoma, sarcoma, etc. Late effects of chemotherapy depend upon the drug and may cause the following: 1) alkylating agents (e.g., cyclophosphamide, chlorambucil, bisulfan, procarbazine, etc.)—hypogonadism, early menopause, acute myeloid leukemia, pulmonary fibrosis, bladder fibrosis, renal failure, etc., 2) cisplatin/carboplatin—hearing loss, vertigo, tinnitis, renal failure, etc., 3) methotrexate—neurocognitive deficits, 4) anthracyclines (e.g., doxorubacin, daunorubicin, etc.)—cardiomyopathy, arrhythmia, and 4) bleomycin—interstitial pneumonitis, pulmonary fibrosis, 5) corticosteroids—osteopenia, osteoporosis, avascular necrosis, 6) epepodophylloxins—acute myeloid leukemia. (Oeffinger K C, Hudson M M. *Long-term complications following childhood and adolescent cancer: foundations for providing risk-based health care for survivors*. CA Cancer J Clin 2004; 54(4):208-236.)

In summary, periodic acceleration has a place in management of cancer either as a stand-alone modality or complimentary to radiotherapy and chemotherapy regimens. Periodic acceleration evokes widespread release of nitric oxide throughout body—wherever there is a blood vessel, pulsatile shear stress promotes expression of nitric oxide that suppresses directly or indirectly pro-tumorigenic mediators. These include nuclear factor kappa beta, vascular endothelial growth factor, inteleukin-8, epidermal growth factor receptor, tumor necrosis superfamily, inducible nitric oxide synthase, mutated p53, COX2, and adhesion molecules. Periodic acceleration does not harm healthy cells nor produce deleterious side effects in contrast to radiotherapy and chemotherapy thereby avoiding the late fibrotic effects of radiation and chemotherapy on normal tissues. Periodic acceleration cannot cause overdose of endothelial-derived mediators. Periodic acceleration is complementary to conventional cancer therapies without adverse "drug" interactions." Periodic acceleration is synergistic or additive in suppression of tumorigenesis to radiotherapy and chemotherapy. Periodic acceleration mitigates the early and late complications of radiotherapy and chemotherapy. Periodic acceleration may be utilized chronically as a cancer prevention measure. Vitamin supplements, antioxidants, and phytochemicals in conjunction with periodic acceleration may increase the effectiveness of NO release from eNOS, with potential for greater suppression of nuclear factor kappa beta and other inflammatory mediators in tumors.

B. Preconditioning and/or Conditioning

Stretch-induced muscle injuries or strains, muscle contusions and delayed-onset muscle soreness (DOMS) are common muscle problems in athletes. Anti-inflammatory treatment is often used for the pain and disability associated with these injuries. The most recent studies on non-steroidal anti-inflammatory drugs (NSAIDs) in sprains and contusions suggest that their use can result in a modest inhibition of the initial inflammatory response and its symptoms. This may be associated with slight negative effects later in the healing phase. Corticosteroids have generally been shown to adversely affect the healing of these acute injuries. The beneficial effect of NSAIDs on improvement of delayed-onset of muscle soreness appears to be minimal. (Almekinders L C. *Anti-inflammatory treatment of muscular injuries in sport. An update of recent studies*, Sports Med 1999; 28:383-88). Prolonged and strenuous exercise induces significant increases in plasma IL-1beta, IL-6 and tumor necrosis factor alpha (Brenner I K, Natale V M, Vasiliou P, Moldoveanu A I, Shek P N, Shephard R J. *Impact of three different types of exercise on components of the inflammatory response*, Eur. J. Appl. Physiol. Occup. Physiol. 1999; 80:452-60; Bruunsgaard H, Galbo H, Halkjaer-Kristensen J, Johansen T L, MacLean D A, Pedersen B K. *Exercise-induced increase in serum interleukin-6 in humans is related to muscle damage*, J. Physiol 1997; 499 (Pt 3):833-41; Pedersen B K, Ostrowski K, Rohde T, Bruunsgaard H. *The cytokine response to strenuous exercise*. Can. J. Physiol. Pharmacol. 1998; 76:505-11).

There is a positive correlation between elevated serum IL-6 levels and skeletal muscle damage in terms of creatine kinase elevations (Bruunsgaard H, Galbo H, Halkjaer-Kristensen J, Johansen T L, MacLean D A, Pedersen B K. *Exercise-induced increase in serum interleukin-6 in humans is related to muscle damage*, J. Physiol. 1997; 499 (Pt 3):833-41). In football players who require intravenous hydration for muscle cramps after training sessions, all have extremely high levels of serum nitrite, presumably released from iNOS present in macrophages and leucocytes as a result of the stress of strenuous exercise (Maddali S, Rodeo S A, Barnes R, Warren R F, Murrell G A. *Postexercise increase in nitric oxide in football players with muscle cramps*. Am. J. Sports Med. 1998; 26:820-24). Athletes seem to be more prone to upper respiratory viral infections probably because strenuous exercise promotes increase of IL-6, tumor necrosis factor alpha, and large quantities of nitric oxide that compromise the immune defense system. These infections usually appear after exercise discontinuation (within 3 days) particularly in those athletes practicing sports that require a long term effort and resistance (Gani F, Passalacqua G, Senna G, Mosca F M. *Sport, immune system and respiratory infections*, Allerg. Immunol. (Paris) 2003; 35:41-46).

Small quantities of nitric oxide released from eNOS suppress strenuous exercise induced activation of nuclear factor kappa beta thereby diminishing IL-1beta, IL-6, tumor necrosis factor and other inflammatory cytokines and adhesion molecules. In addition, small quantities of nitric oxide from eNOS suppress activity of iNOS (Stefano G B, Prevot V, Cadet P, Dardik I. *Vascular pulsations stimulating nitric oxide release during cyclic exercise may benefit health: a molecular approach (review)*. Int. J. Mol. Med. 2001; 7:119-29). This is important because large amounts of nitric oxide are released after strenuous exercise in professional football players and other athletes that are associated with severe muscle cramps.

Therefore, periodic acceleration can mitigate skeletal muscular cramps during an athletic event, and help to prevent muscle strains during an event as well as delayed onset muscular soreness (DOMS) and involuntary muscle cramps and spasms immediately following the athletic event and delayed until the sleeping hours. It has been found that an additional periodic acceleration treatment administered four to eight hours after the athletic event provides even better relief than a single pretreatment in relieving nocturnal muscle cramps.

In addition to skeletal muscle damage and propensity to viral infections associated with strenuous exercise, damage to heart muscle may occur even in normal subjects. Cardiac troponin T (cTnT) and troponin I (cTnI) are highly sensitive and specific for detecting myocardial damage even in the presence of skeletal muscle injury. Ultraendurance exercise may cause myocardial damage as indicated by elevations of these biochemical cardiac-specific markers and also by echocardiography (Rifai N, Douglas P S, O'Toole M, Rimm E, Ginsburg G S. *Cardiac troponin T and I, echocardiographic [correction of electrocardiographic] wall motion analyses, and ejection fractions in athletes participating in the Hawaii Ironman Triathlon*, Am. J. Cardiol. 1999; 83:1085-89; Shave R E, Dawson E, Whyte G, George K, Ball D, Gaze D C et al. *Evidence of exercise-induced cardiac dysfunction and elevated cTnT in separate cohorts competing in an ultra-endurance mountain marathon race* Int. J. Sports Med. 2002: 23:489-94; Ohba H, Takada H, Musha H, Nagashima J, Mori N, Awaya T et al. *Effects of prolonged strenuous exercise on plasma levels of atrial natriuretic peptide and brain natriuretic peptide in healthy men*, Am. Heart J. 2001; 141:751-58). There are no studies reported in the literature on normal subjects with regard to less strenuous exercise but it stands to reason that in some individuals, minor damage might occur. Minimal myocardial damage could compromise athletic performance.

Activation of eNOS to release small quantities of nitric oxide preconditions the heart against the adverse effects of compromise of the blood supply to the heart that produces myocardial damage. Periodic acceleration activates eNOS through increased pulsatile shear stress and, as such, is a means to precondition the heart. Endogenous nitric oxide 1) reduces myocardial oxygen consumption and thus improves regional myocardial function for any given level of myocardial blood flow, oxygen consumption and energetics, 2) preserves contractile calcium sensitivity during myocardial ischemia, and 3) contributes to hibernation, i.e., adaptation to myocardial ischemia, by preserving regional contractile function without any effect on myocardial energetics (Heusch G, Post H, Michel M C, Kelm M, Schulz R. *Endogenous nitric oxide and myocardial adaptation to ischemia*. Circ. Res. 2000; 87:146-52). Since the limitation to athletic activities often is the amount of blood pumped by the heart through the body, preconditioning with periodic acceleration serves to optimize athletic performance.

Based upon animal experiments, upregulation of endothelial nitric oxide synthase activity should increase the number of mitochondria present in skeletal muscle cells. In turn, heat production is increased within these cells thereby improving sports performances. (Nisoli E, Clementi E, Paolucci C et al. *Mitochondrial biogenesis in mammals: the role of endogenous nitric oxide*. Science 2003; 299(5608):896-899; Brown G C. NO says YES to mitochondria. Science 2003; 299:838-839.)

Exercise-induced bronchospasm (EIB), i.e., an asthmatic episode, affects up to 35% of athletes and up to 90% of asthmatics (Kukafka D S, Lang D M, Porter S, Rogers J, Ciccolella D, Polansky M et al., *Exercise-induced bronchospasm in high school athletes via a free running test: incidence and epidemiology*. Chest 1998; 114:1613-22). This factor limits athletic capabilities.

Since many athletic venues do not permit effective drugs for the treatment of asthma because of they also improve performance unrelated to alleviation of asthma, pretreatment of such athletes can be accomplished with periodic acceleration to prevent exercise induced asthma. Here, the beneficial agent, nitric oxide is generated from the athlete's own body.

Physical activity protects against ischemic stroke via mechanisms related to the upregulation of endothelial nitric oxide synthase (eNOS) in the vasculature. In wild-type mice that performed voluntary training on running wheels or exercise on a treadmill apparatus for 3 weeks, respectively, ligation of the middle cerebral artery was associated with reduced cerebral infarct size and functional deficits, improved endothelium-dependent vasorelaxation, and augmented cerebral blood flow. The neuroprotective effects of physical training were completely absent in eNOS-deficient mice, indicating that the enhanced eNOS activity by physical training was the predominant mechanism by which this modality protects against cerebral injury. (Endres M, Gertz K, Lindauer U et al. *Mechanisms of stroke protection by physical activity*. Ann Neurol 2003; 54(5):582-590.)

In summary, periodic acceleration treatments administered prior to an athletic event minimize delayed onset of muscle soreness (DOMS) and nocturnal muscle spasms. An additional periodic acceleration treatment administered four to eight hours following cessation of the athletic event provides even further relief. Periodic acceleration administered prior to strenuous athletic events minimizes microscopic myocardial damage. Chronic treatment with periodic acceleration improves sports performance by promoting mitochondrial biogenesis. Periodic acceleration administered prior to an athletic event protects against exercise induced asthma. Since many athletic venues do not permit effective drugs for the treatment of asthma because of they also improve performance unrelated to alleviation of asthma, pretreatment of competitive athletes can be accomplished with periodic acceleration to prevent exercise induced asthma. Chronic periodic acceleration treatments should minimize damage that might occur with ischemic events such as stroke, coronary thrombosis, pulmonary embolism, etc.

C. Weight Control

An epidemic of obesity exists in the United States and other countries of the Western World. Currently, 65% of American adults are overweight and 31% are obese. Further, this prevalence parallels the 29% prevalence of hypertension with blood pressures >140/90 or taking anti-hypertensive drugs. Weight loss is critical in the effective management of obesity hypertension and the accompanying target organ damage, although recidivism rates are high. Prevention of weight gain should be the major priority for combating hypertension and its consequences in the future. (Davy K P, Hall J E. Obesity and hypertension: two epidemics or one? Am J Physiol Regul Integr Comp Physiol 2004; 286(5):R803-R813.) Depression and obesity are linked to elevated CRP suggesting a possible synergistic effect of obesity and depressive mood on chronic low-level inflammation, which may play a crucial role in the pathogenesis of atherosclerosis. (Ladwig K H, Marten-Mittag B, Lowel H et al. *Influence of depressive mood on the association of CRP and obesity in* 3205 *middle aged healthy men*. Brain Behav Immun 2003; 17(4):268-275.) Exercise and proper diet are key to weight control but numerous studies have stressed the difficulty in getting obese patients to comply.

In a one year study, it was found that nitric oxide deficient mice (eNOS knockout) were significantly heavier than normal wild-type mice over the entire observation period even though dietary intake and activity were controlled and the same. The NO deficient had lesser oxygen consumptions and fewer mitochondria in brown adipocytes than the wild type mice. The investigators concluded that eNOS regulates mitochondrial biogenesis, energy expenditure and heat production. They noted that NOS deficiency reduced energy expenditure and produced weight gain, insulin resistance, and hypertension, which are typical features of the metabolic syndrome. (Nisoli E, Clementi E, Paolucci C et al. *Mitochondrial biogenesis in mammals: the role of endogenous nitric oxide*. Science 2003; 299(5608):896-899.) Based upon these findings, Brown speculated that if eNOS could be upregulated, then an increase mitochondrial number in skeletal muscle would increase sport performances, reduce obesity, treat the metabolic syndrome and even reverse aging. (Brown G C. *NO says YES to mitochondria*. Science 2003; 299:838-839.) I have made anecdotal observations in three subjects indicating that two, 45 minute treatments daily with periodic acceleration cause significant weight reduction over weeks to months period. A metabolic chamber study in a single subject using periodic acceleration produced an excess caloric expenditure of approximately 100 calories in 24 hours compared to a control day. Long term periodic acceleration should produce an accumulative effect as a result of increased mitochondrial biogenesis. Thus, periodic acceleration ought to play a role in the management of obesity.

Cachexia, which is marked by severe weight loss, is the opposite of obesity yet it too may respond to upregulation of eNOS but by a totally different mechanism. For example, weight loss, mostly due to skeletal muscle atrophy, is a frequent and clinically relevant problem in patients with chronic obstructive pulmonary disease (COPD) as well as in patients with neoplasms. In such patients, activation of nuclear factor kappa beta and iNOS induction takes place in the skeletal muscle and contributes to the molecular pathogenesis of cachexia along with other inflammatory cytokines. (Agusti A, Morla M, Sauleda J et al. *NF-kappaB activation and iNOS upregulation in skeletal muscle of patients with COPD and low body weight*. Thorax 2004; 59(6):483-487) Periodic acceleration by increasing release of small amounts of nitric oxide from eNOS suppresses nuclear factor kappa beta and iNOS activities thereby ameliorating the skeletal muscle pathology. In addition, deficiency of eNOS causes less muscle oxidative capacity as well as the activities of energy metabolism enzymes in oxidative (soleus) muscle. (Momken I, Fortin D, Serrurier B et al. *Endothelial nitric oxide synthase (NOS) deficiency affects energy metabolism pattern in murine oxidative skeletal muscle*. Biochem J 2002; 368(Pt 1):341-347.) This, too, is ameliorated with upregulation of eNOS by periodic acceleration.

In summary, periodic acceleration treatments control weight, ameliorate the metabolic syndrome, improve sports performance, and improve skeletal muscle pathology associated with the cachexia of COPD and cancers.

D. Ventricular Remodeling

While current therapeutic strategies are designed to restore blood flow to the ischemic myocardium and limit infarct size, adverse left ventricular remodeling progressing to dysfunction remains a significant complication following myocardial infarction. Ventricular remodeling also takes place in conditions associated with volume overload. Ventricular remodeling consists of change from an elliptical to a spherical left ventricular volume with concomitant increase of end-systolic and end-diastolic diameters. Reverse remodeling means a reversal of ventricular shape toward a normal shape. In myocardial infarctions, the extracellular matrix (ECM) is a key component in the remodeling process through increases of collagen in the infarct area that replace necrotic myocytes to form a scar. In addition, the matrix metalloproteinases (MMP) coordinate ECM turnover through degradation of ECM components. Several laboratories have demonstrated that MMP participates in remodeling events that lead to left ventricular dilation, and inhibition or targeted deletion of specific MMPs has beneficial effects post-myocardial infarction. (Lindsey M L, Mann D L, Entman M L et al. *Extracellular matrix remodeling following myocardial injury*. Ann Med 2003; 35(5):316-326) Left ventricular remodeling that occurs in mitral regurgitation and other ventricular volume overload conditions are produced by overstretch of the myocardium. (Oral H, Sivasubramanian N, Dyke D B et al. *Myocardial proinflammatory cytokine expression and left ventricular remodeling in patients with chronic mitral regurgitation*. Circulation 2003; 107(6):831-837; Wei C C, Lucchesi P A, Tallaj J et al. *Cardiac interstitial bradykinin and mast cells modulate pattern of LV remodeling in volume overload in rats*. Am J Physiol Heart Circ Physiol 2003; 285(2):H784-H792; Stewart J A, Jr., Wei C C, Brower G L et al. *Cardiac mast cell- and chymase-mediated matrix metalloproteinase activity and left ventricular remodeling in mitral regurgitation in the dog*. J Mol Cell Cardiol 2003; 35(3):311-319.)

Several mediators regulate ventricular remodeling. Over stretch of the myocardium due to volume overload causes expression of tumor necrosis factor alpha. (Oral H, Sivasubramanian N, Dyke D B et al. *Myocardial proinflammatory cytokine expression and left ventricular remodeling in patients with chronic mitral regurgitation*. Circulation 2003; 107(6):831-837.) As mentioned above, MMP's activity increases during ventricular remodeling. In experimental aortocaval fistula in rats, the number of myocardial mast cells significantly increases, and there is a close association between mast cell density and MMP activity. Cromolyn, a drug that inhibits degranulation of the mast cell prevents the increase in mast cell number and MMP activity. Therefore cardiac mast cells play a major role in regulating MMP activity in ventricular remodeling. (Brower G L, Chancey A L, Thanigaraj S et al. *Cause and effect relationship between myocardial mast cell number and matrix metalloproteinase activity*. Am J Physiol Heart Circ Physiol 2002; 283(2):H518-H525.) Further, there is a significant interaction of mast cells and bradykinin in the cardiac interstitium that modulates the pattern of LV remodeling in the acute phase of volume overload. (Wei C C, Lucchesi P A, Tallaj J et al. *Cardiac interstitial bradykinin and mast cells modulate pattern of LV remodeling in volume overload in rats*. Am J Physiol Heart Circ Physiol 2003; 285(2):H784-H792.) Cardiac mast cells and chymase are important modulators of MMP activity and extracellular matrix degradation that contribute to adverse left ventricular remodeling in chronic volume overload secondary to mitral regurgitation. (Stewart J A, Jr., Wei C C, Brower G L et al. *Cardiac mast cell- and chymase-mediated matrix metalloproteinase activity and left ventricular remodeling in mitral regurgitation in the dog*. J Mol Cell Cardiol 2003; 35(3):311-319.)

Another mediator that promotes ventricular remodeling is caspase-3 that is activated by myocardial stunning following myocardial ischemia. (Ruetten H, Badorff C, Ihling C et al. *Inhibition of caspase-3 improves contractile recovery of stunned myocardium, independent of apoptosis-inhibitory effects*. J Am Coll Cardiol 2001; 38(7):2063-2070.) Caspase-3 promotes cleavage of troponin-I, an important component of the cardiac contractile apparatus, and death or apoptosis of cardiomyocytes. Inhibition of caspase-3 by pharmacological agents causes less cleavage of tropomin-1 and fewer apoptotic cardiomyocytes. This intervention in turn preserves myocardial contractile proteins, reduces systolic dysfunction, and attenuates ventricular remodeling. (Chandrashekhar Y, Sen S, Anway R et al. *Long-term caspase inhibition ameliorates apoptosis, reduces myocardial troponin-I cleavage, protects left ventricular function, and attenuates remodeling in rats with myocardial infarction*. J Am Coll Cardiol 2004; 43(2):295-301.) Nitric oxide from eNOS tonically inhibits myocardial caspase activity and prevents caspase activation by upstream caspases. The ability of NO to inhibit downstream caspase 3 has potential to rescue a cell from apoptosis (programmed cell death) even after the caspase cascade has been activated. The reduced NO in chronic heart failure increases myocardial caspase 3 activity. Agents that promote NO release from eNOS such as ACE inhibitors, prevent caspase activation in heart failure and attenuate ventricular remodeling. (Mital S, Barbone A, Addonizio L J et al. Endogenous endothelium-derived nitric oxide inhibits myocardial caspase activity: implications for treatment of end-stage heart failure. J Heart Lung Transplant 2002; 21(5):576-585.)

Left ventricular reverse remodeling takes place in animals after administration of drugs that increase activity of eNOS. (Kobayashi N, Mori Y, Nakano S et al. *Celiprolol stimulates endothelial nitric oxide synthase expression and improves myocardial remodeling in deoxycorticosterone acetate-salt hypertensive rats*. J Hypertens 2001; 19(4):795-801; Kobayashi N, Hara K, Watanabe S et al. *Effect of imidapril on myocardial remodeling in L-NAME-induced hypertensive rats is associated with gene expression of NOS and ACE mRNA*. Am J Hypertens 2000; 13(2):199-207.) In humans, cardiac resynchronization therapy produces reverse left ventricular (LV) remodeling in patients with congestive heart failure that might be due to upregulation of eNOS. (Penicka M, Bartunek J, De Bruyne B et al. *Improvement of left ventricular function after cardiac resynchronization therapy is predicted by tissue Doppler imaging echocardiography*. Circulation 2004; 109(8):978-983; Hiratsuji T, Adachi H, Isobe N et al. [Does cardiac resynchronization therapy improve nitric oxide concentration in exhaled gas?]. J Cardiol 2004; 43(1):11-15.)

Periodic acceleration through release of NO from eNOS promotes left ventricular reverse remodeling because it suppresses the activity of several mediators that play in role in promoting left ventricular remodeling including tumor necrosis factor alpha and caspase-3. Periodic acceleration also prevents cardiac mast cell degranulation as a result of the increased nitric oxide from eNOS. In this respect, heparin also prevents mast cell degranulation and activated eNOS to release NO. (Kouretas P C, Hannan R L, Kapur N K et al. *Non-anticoagulant heparin increases endothelial nitric oxide synthase activity: role of inhibitory guanine nucleotide proteins*. J Mol Cell Cardiol 1998; 30(12):2669-2682. Finally, periodic acceleration causes a significant increase of myocardial blood flow that suppresses adverse mediator expression. (Adams J A, Mangino M J, Bassuk J et al. *Regional blood flow during periodic acceleration*. Crit Care Med 2001; 29(10):1983-1988.)

In summary, periodic acceleration administered early in situations that promote left ventricular remodeling such as acute myocardial infarction and ventricular volume overload from mitral regurgitation, aortic regurgitation and arteriovenous fistula attenuates ventricular remodeling. Administration of periodic acceleration after ventricular remodeling has developed promotes beneficial reverse ventricular remodeling. The combination of periodic acceleration with drugs that stabilize cardiac mast cells such as non-coagulant and coagulant heparin and cardiac drugs that activate eNOS such as ACE inhibitors as well as heparin produce additive or synergistic effects.

E. Atrial Fibrillation

Atrial fibrillation may occur in susceptible patients as a result of electrical remodeling of the atria due to oxidative stress or inflammation. (Korantzopoulos P, Kolettis T, Siogas K et al. *Atrial fibrillation and electrical remodeling: the potential role of inflammation and oxidative stress*. Med Sci Monit 2003; 9(9):RA225-RA229.) In this respect, statins have been shown to prevent atrial fibrillation in patients with coronary artery disease independent of their cholesterol lowering properties. (Young-Xu Y, Jabbour S, Goldberg R et al. *Usefulness of statin drugs in protecting against atrial fibrillation in patients with coronary artery disease*. Am J Cardiol 2003; 92(12):1379-1383.) Further, stains promote release of nitric oxide from eNOS, and NO has potent anti-inflammatory and anti-oxidative stress effects. (Laufs U. *Beyond lipid-lowering: effects of statins on endothelial nitric oxide*. Eur J Clin Pharmacol 2003; 58(11):719-731.) Thus, chronic periodic acceleration treatments that upregulation of eNOS activity prevents or minimizes occurrence of atrial fibrillation.

Atrial fibrillation is associated with decreased expression of eNOS in left atrial tissue because of turbulent flow in the atrium. Decreased NO is associated with lack of inhibition of prothrombotic protein plasminogen activator inhibitor-1 (PAI-1) and therefore predisposes to atrial thrombus formation, a serious complication that can lead to stroke. (Cai H, Li Z, Goette A et al. *Downregulation of endocardial nitric oxide synthase expression and nitric oxide production in atrial fibrillation: potential mechanisms for atrial thrombosis and stroke*. Circulation 2002; 106(22):2854-2858.)

In summary, chronic periodic acceleration treatments is patients susceptible to atrial fibrillation because of enlarged left atrium, e.g., mitral stenosis, mitral regurgitation, chronic heart failure, can be administered prophylactically. In established atrial fibrillation, chronic periodic acceleration can prevent the formations of left atrial thrombosis.

F. Coronary Artery Bypass Surgery

Myocardial tumor necrosis factor alpha production and nuclear factor kappa B activation has been demonstrated in chronic heart failure and experimental models of acute ischemia-reperfusion injury. Further, a cause and effect relationship has been established between these events and cardiomyocyte apoptosis (cell death) following such conditions. Recently, it as found that coronary artery bypass grafting results in activation of NF-kappaB and an increase of tumor necrosis factor alpha in the heart. (Meldrum D R, Partrick D A, Cleveland J C, Jr. et al. *On-pump coronary artery bypass surgery activates human myocardial NF-kappaB and increases TNF-alpha in the heart*. J Surg Res 2003; 112(2): 175-179.) These mediators promote the deleterious effect of inflammation from cardiopulmonary bypass (CPB) is known to cause part of the systemic inflammatory reaction after cardiac surgery that lead to organ failure. (Fillinger M P, Rassias A J, Guyre P M et al. *Glucocorticoid effects on the inflammatory and clinical responses to cardiac surgery*. J Cardiothorac Vasc Anesth 2002; 16(2):163-169.)

After coronary artery bypass surgery, almost a quarter of patients have a cognitive deficit when tested two months after the operation. This improves but cognitive deficit can be detected in some patients even five years later. (van Dijk D, Kaiser A M, Daphnis J C et al. *Neurocognitive dysfunction after coronary artery bypass surgery: a systematic review*. J Thorac Cardiovasc Surg 2000; 120(4):632-639; Stygall J, Newman S P, Fitzgerald G et al. *Cognitive change 5 years after coronary artery bypass surgery*. Health Psychol 2003; 22(6):579-586.) This cognitive deficit has been attributed to cerebral microembolism. Nitric oxide released from eNOS improves red cell deformability permitting easier capillary passage. (Bor-Kucukatay M, Wenby R B, Meiselman H J et al. *Effects of nitric oxide on red blood cell deformability*. Am J Physiol Heart Circ Physiol 2003; 284(5):H1577-H1584.

Long-term potentiation (LTP) is a persistent increase in synaptic strength of nerves implicated in certain forms of learning and memory. eNOS from endothelial cells, rather than nNOS, generates NO within the postsynaptic cell in the central nervous system in LTP. (Blackshaw S, Eliasson M J, Sawa A et al. *Species, strain and developmental variations in hippocampal neuronal and endothelial nitric oxide synthase clarify discrepancies in nitric oxide-dependent synaptic plasticity*. Neuroscience 2003; 119(4):979-990; O'Dell T J, Huang P L, Dawson T M et al. *Endothelial NOS and the blockade of LTP by NOS inhibitors in mice lacking neuronal NOS*. Science 1994; 265(5171):542-546.) Increased eNOS activity within the brain promotes long-term potentiation at cortico-striatal connections thereby favoring memory and learning. Blockade of eNOS activity in chicks impairs memory. (Doreulee N, Sergeeva O A, Yanovsky Y et al. *Cortico-striatal synaptic plasticity in endothelial nitric oxide synthase deficient mice*. Brain Res 2003; 964(1):159-163; Rickard N S, Gibbs M E, Ng K T. *Inhibition of the endothelial isoform of nitric oxide synthase impairs long-term memory formation in the chick*. Learn Mem 1999; 6(5):458-466.) Recently, it has been found that LTP may take place in connections to the hypoglossal nerve, which controls tongue movements. Long-term depression of such activity may contribute to the pathogenesis of the obstructive sleep apnea syndrome. (Bocchiaro C M, Feldman J L. *Synaptic activity-independent persistent plasticity in endogenously active mammalian motoneurons*. Proc Natl Acad Sci USA 2004; 101(12):4292-4295.)

In summary, periodic acceleration by releasing NO from eNOS plays a major role in management of complications of coronary artery bypass surgery. In addition to preconditioning the heart to the adverse effects of ischemia described in another section above, periodic acceleration treatments administered prior to and after coronary artery bypass surgery attenuate the inflammatory effects of cardiopulmonary bypass that can lead to the systemic inflammatory response and organ failure. Periodic acceleration treatments administered prior to and after coronary artery bypass surgery can mitigate the cognitive and learning deficits that are common after cardiopulmonary bypass surgery in part by improving red cell deformability with easier capillary passage. Periodic acceleration treatments can attenuate the obstructive sleep apnea syndrome commonly observed in patients with coronary artery disease.

G. Cognitive and Learning Impairment in Movement Disorders

Treatments with periodic acceleration also improve cognitive impairments and dementia because nitric oxide released from eNOS improves cerebral blood flow and long-term potentiation (LTP), a persistent increase in synaptic strength of nerves implicated in certain forms of learning and memory as described above. This is of particular importance in management of mild cognitive impairment, defined as memory complaints with objective memory impairment, without dementia, impairment of general cognitive functioning, or disability in activities of daily living. In a large population study, this was a good predictor of Alzheimer's disease with an annual conversion rate of 8.3% and good specificity, but very unstable over time: Within 2 to 3 years, only 6% of the subjects continued to have MCI, whereas >40% reverted to normal. (Larrieu S, Letenneur L, Orgogozo J M et al. *Incidence and outcome of mild cognitive impairment in a population-based prospective cohort*. Neurology 2002; 59(10): 1594-1599; Voisin T, Touchon J, Vellas B. *Mild cognitive impairment: a nosological entity? Curr Opin Neurol* 2003; 16 Suppl 2:S43-S45.) Mild cognitive impairment refers to the transitional zone between normal ageing and dementia and may be the optimum stage to intervene with preventive therapies such as periodic acceleration.

Cognitive dysfunction is a major component of several neurological diseases such as Alzheimer's disease and vascular dementia. (De La Torre J C. *Alzheimer's disease is a vasocognopathy: a new term to describe its nature*. Neurol Res 2004; 26(5):517-524.) In its earliest clinical phase, Alzheimer's disease characteristically produces a remarkably pure impairment of memory. Mounting evidence suggests that this syndrome begins with subtle alterations of hippocampal synaptic efficacy prior to frank neuronal degeneration, and that diffusible oligomeric assemblies of the amyloid beta protein cause the synaptic dysfunction. (Selkoe D J. *Alzheimer's disease is a synaptic failure*. Science 2002; 298 (5594):789-791.) Patients with Parkinson's disease can also exhibit cognitive and behavioral impairments. These impairments may be attributed to dysfunction of multiple systems associated with the disease process in Parkinson's disease that are not necessarily related to motor symptoms. In recent years, considerable attention has addressed to disruption of the circuits in patients with Parkinson's disease connecting the frontal cortical regions and the basal ganglia (i.e., frontostriatal circuits) and how they mediate cognition and behavior in humans. (Zgaljardic D J, Borod J C, Foldi N S et al. *A review of the cognitive and behavioral sequelae of Parkinson's disease: relationship to frontostriatal circuitry*. Cogn Behav Neurol 2003; 16(4):193-210.) Recently, it has been recognized that cognitive decline may be present in a population of patients with amyotrophic lateral sclerosis. (Strong M, Rosenfeld J. *Amyotrophic lateral sclerosis: a review of current concepts*. Amyotroph Lateral Scler Other Motor Neuron Disord 2003; 4(3):136-143.) Frontalstriatal synaptic circuits are disrupted in an animal model of ALS. (Geracitano R, Paolucci E, Prisco S et al. *Altered long-term corticostriatal synaptic plasticity in transgenic mice overexpressing human CU/ZN superoxide dismutase* (GLY(93)—>ALA) mutation. Neuroscience 2003; 118(2):399-408.) Frontalstrial synapses are also disrupted in other movement disorders such as Huntington's chorea and Wilson's disease in animal models, probably suprabulbar palsy and possibly Tourette syndrome. (Murphy K P, Carter R J, Lione L A et al. *Abnormal synaptic plasticity and impaired spatial cognition in mice transgenic for exon* 1 *of the human Huntington's disease mutation*. J Neurosci 2000; 20(13):5115-5123; Doreulee N, Yanovsky Y, Haas H L. *Suppression of long-term potentiation in hippocampal slices by copper*. Hippocampus 1997; 7(6):666-669; Clark M, Carr L, Reilly S et al. *Worster-Drought syndrome, a mild tetraplegic perisylvian cerebral palsy*. Review of 47 cases. Brain 2000; 123 (Pt 10):2160-2170; Albin R L, Koeppe R A, Bohnen N I et al. *Increased ventral striatal monoaminergic innervation in Tourette syndrome*. Neurology 2003; 61(3):310-315.)

Thus, frontalstriatal circuits appear to be disrupted or impaired in Alzheimer's disease, vascular dementia Parkinson's disease and amyotrophic lateral sclerosis, Huntington's chorea, Wilson's disease, suprabulbar palsy thereby causing memory and learning deficits association with long term depression of the synaptic pathways. Long-term potentiation (LTP), a persistent increase in synaptic strength is favorable for certain forms of learning and memory. It has been found that eNOS from endothelial cells, rather than nNOS, generates NO within the postsynaptic cell as a means of producing LTP. (O'Dell T J, Huang P L, Dawson T M et al. *Endothelial NOS and the blockade of LTP by NOS inhibitors in mice lacking neuronal NOS*. Science 1994; 265(5171):542-546.) Therefore, activation of eNOS with release of nitric oxide attendant with periodic acceleration treatments improves memory, learning and behavior in patients with Alzheimer's disease, vascular dementias, Parkinson's disease, amyotrophic lateral sclerosis, Huntington's chorea, Wilson's disease, suprabubar palsy and possibly Tourette syndrome.

Impairment of NO-synthesis in eNOS deficient mice shifts striatal plasticity from long term potentiation to long term depression. Since computation of perivascular NO gradients from the vessel wall of capillaries indicates that targets 200 um distant can still be reached by NO, this is consistent with the possibility that NO released from eNOS participates in the modulation of cortico-striatal plasticity. (Doreulee N, Sergeeva O A, Yanovsky Y et al. *Cortico-striatal synaptic plasticity in endothelial nitric oxide synthase deficient mice*. Brain Res 2003; 964(1):159-163.) Further, this assertion is consistent with the rapid, dramatic improvements observed after only one 45 minute periodic acceleration treatment in patients with these movement disorders. The added pulses produced with periodic acceleration is superior to nonpulsatile blood flow. Thus, Baba et al used a pump to bypass the heart that produced pulsatile and nonpulsatile flow in goats and observed bulbar conjunctiva capillaries with a digital high definition microscope. When the flow pattern was changed from pulsatile to nonpulsatile, the velocity of erythrocytes in many capillaries dropped and remained at a low level, and the number of perfused capillaries decreased. After the flow pattern was returned to pulsatile, the velocity of erythrocytes recovered to the initial level. In many cases, the flow of nonperfused capillaries recovered to the initial level as well. Also, pulsatile flow enhanced the basal and flow-stimulated endothelium-derived nitric oxide release in the microvessels. (Baba A, Dobsak P, Mochizuki S et al. *Evaluation of pulsatile and nonpulsatile flow in microvessels of the bulbar conjunctiva in the goat with an undulation pump artificial heart*. Artif Organs 2003; 27(10):875-881.

In summary, periodic acceleration is indicated as prophylactic and therapeutic treatment for cognitive and learning deficits as well as behavioral abnormalities in early cognitive impairment, Alzheimer's disease, vascular dementias, Parkinson's disease, amyotrophic lateral sclerosis, Huntington's chorea, Wilson's disease, suprabulbar palsy and possibly Tourette syndrome.

H. Cardiac Allograph Vasculopathy

Accelerated graft atherosclerosis is a key feature of most chronic rejection syndromes. Atherosclerosis diffusely involves the coronary circulation. Cardiac allograft vasculopathy is the most aggressive form of atherosclerosis in humans and is the leading cause of death after the first year of heart transplantation. Endothelial dysfunction is a major contributing factor to the acceleration of coronary vascular disease in these individuals. Alteration in endothelial function contributes to vascular inflammation and progression of the disease. (Weis M, Cooke J P. *Cardiac allograft vasculopathy and dysregulation of the NO synthase pathway*. Arterioscler Thromb Vasc Biol 2003; 23(4):567-575.). Periodic acceleration ameliorates the endothelial dysfunction responsible for this syndrome.

I. Endothelial Progenitor Cells

Endothelial nitric oxide synthase (eNOS) is essential for neovascularization. Impaired neovascularization in mice lacking eNOS is related to a defect in progenitor cell mobilization owing to reduced vascular endothelial growth factor (VEGF)-induced mobilization of endothelial progenitor cells (EPCs). eNOS expressed by bone marrow stromal cells in response to shear stress influences recruitment of stem and progenitor cells. This may contribute to impaired regeneration processes in ischemic heart disease patients, who are characterized by a reduced systemic NO bioactivity. Aerobic exercise by release of NO from eNOS increases vascular endothelial growth factor (VEGF) with consequent increase of endothelial progenitor cells. (Aicher A, Heeschen C, Mildner-Rihm C et al. *Essential role of endothelial nitric oxide synthase for mobilization of stem and progenitor cells*. Nat Med 2003; 9(11):1370-1376; Laufs U, Werner N, Link A et al. *Physical training increases endothelial progenitor cells,*

*inhibits neointima formation, and enhances angiogenesis*. Circulation 2004; 109(2):220-226.) C-Reactive Protein (CRP) at concentrations > or =15 microg/mL significantly reduces the number of EPC's. Human recombinant CRP, at concentrations known to predict adverse vascular outcomes, directly inhibits EPC differentiation, survival, and function, key components of angiogenesis and response to chronic ischemia. This occurs in part because CRP reduces EPC eNOS expression. (Verma S, Kuliszewski M A, Li S H et al. *C-reactive protein attenuates endothelial progenitor cell survival, differentiation, and function: further evidence of a mechanistic link between C-reactive protein and cardiovascular disease*. Circulation 2004; 109(17):2058-2067.)

Periodic acceleration like aerobic exercise promotes mobilization of endothelial progenitor cells into the circulation as well as suppression of CRP if elevated. Periodic acceleration aids in promoting angiogenesis in ischemic tissues.

J. Hereditary Hemorrhagic Telangiectasis

Hereditary hemorrhagic telanglectasis (Osler-Weber-Rendu disease) is caused by a genetic deficiency of endoglin. Endoglin also regulates transforming growth factor beta 1; In turn this mediator causes under-expression of eNOS that leads to development of abnormal blood flow passages and the manifestations of the disease. These patients experience frequent bleedings with increasing age, in particular from the nasal, gastrointestinal, and cerebral vascular beds. Vascular arteriovenous malformations develop that vary in size from 1 mm to several centimeters. Pulmonary vascular arteriovenous malformations are particularly life threatening because of bleeding. or paradoxical embolism causing brain infarction or brain abscess. The cause of hereditary hemorrhagic telangiectasis is mutated genes identified as endoglin and ALK-1. They mediate binding on signaling of transforming growth factor beta. The disease develops as a result of deficient TGF beta signaling in vascular endothelial cells that produces abnormal blood vessel development. (Jerkic M, Rivas-Elena J V, Prieto M et al. *Endoglin regulates nitric oxide-dependent vasodilatation*. FASEB J 2004; 18(3):609-611; van den D S, Mummery C L, Westermann C J. *Hereditary hemorrhagic telangiectasia: an update on transforming growth factor beta signaling in vasculogenesis and angiogenesis*. Cardiovasc Res 2003; 58(1):20-31.)

Periodic acceleration helps in the management of hereditary hemorrhagic telangiectasia because it addresses the underlying cause of this disease, i.e., under-expression of eNOS.

K. Migraine

Nitric oxide generated from inducible nitric oxide synthase (iNOS) participates in immune and inflammatory responses in many tissues. The NO donor glyceryl trinitrate (GTN) provokes delayed migraine attacks when infused into migraineurs and also causes iNOS expression and delayed inflammation within rodent dura mater. Sodium nitroprusside, an NO donor as well, also increases iNOS expression. Intravenous GTN increases NO production within macrophages. iNOS expression is preceded by significant nuclear factor kappa beta activity after GTN infusion. Nuclear factor kappa beta activation and iNOS expression are attenuated by parthenolide (3 mg/kg), the active constituent of feverfew, an anti-inflammatory drug used for migraine treatment. Thus, GTN promotes NF-kappaB activity and inflammation with a time course consistent with migraine attacks in susceptible individuals. Therefore, blockade of NF-kappaB activity provides a target for the anti-migraine treatment. (Reuter U, Chiarugi A, Bolay H et al. *Nuclear factor-kappaB as a molecular target for migraine therapy*. Ann Neurol 2002; 51 (4):507-516.) Since periodic acceleration causes release of NO from eNOS and NO suppresses activity of nuclear factor kappa beta and iNOS, this action provides effective anti-migraine treatment.

L. Prion Diseases

Prion diseases, Mad Cow and Creutzfeldt-Jakob diseases, are devastating lethal neurological diseases which currently are untreatable. However, examination of brain tissue from these patients reveals inflammation marked by accumulation of COX-1-expressing macrophages/microglial cells and COX-2-expressing neurons, and increased nuclear factor kappa beta and iNOS activity, (Bacot S M, Lenz P, Frazier-Jessen M R et al. *Activation by prion peptide PrP*106-126 *induces a NF-kappaB-driven proinflammatory response in human monocyte-derived dendritic cells*. J Leukoc Biol 2003; 74(1):118-125; Brown D R, Nicholas R S, Canevari L. *Lack of prion protein expression results in a neuronal phenotype sensitive to stress*. J Neurosci Res 2002; 67(2):211-224; Cui T, Holme A, Sassoon J et al. *Analysis of doppel protein toxicity*. Mol Cell Neurosci 2003; 23(1):144-155; Deininger M H, Bekure-Nemariam K, Trautmann K et al. *Cyclooxygenase*-1 *and* -2 *in brains of patients who died with sporadic Creutzfeldt-Jakob disease*. J Mol Neurosci 2003; 20(1):25-30.) Since all these inflammatory mediators are suppressed by nitric oxide released from eNOS during periodic acceleration, this therapy has a place in treating the inflammation attendant with prion diseases.

M. Aging

Reactive oxygen species (ROS) and reactive nitrogen species (RNS) are widely implicated in the inflammatory process. During the aging process, both ROS and RNS are increased along with an inflammatory response that takes place in the body involving upregulation of nuclear factor kappa beta, IL-beta, IL-6, tumor necrosis factor alpha, cyclooxygenase-2, and inducible NO synthase. Caloric restriction downregulates these inflammatory mediators. (Chung H Y, Kim H J, Kim J W et al. *The inflammation hypothesis of aging: molecular modulation by calorie restriction*. Ann NY Acad Sci 2001; 928:327-335.) Activated nuclear factor kappa beta produces oxidative stress via the induction of MnSOD and contributes the ageing process. (Bernard D, Gosselin K, Monte D et al. *Involvement of Rel/nuclear factor-kappaB transcription factors in keratinocyte senescence*. Cancer Res 2004; 64(2):472-481. Chronic inflammation accounts for effects of susceptibility to infection in aged animals. For example, the increased expression of proinflammatory cytokines and inflammatory responsive genes in the lung plays a role in the increased susceptibility in aging animals to endotoxic stress. (Chang C K, LoCicero J, III. *Overexpressed nuclear factor kappaB correlates with enhanced expression of interleukin*-1*beta and inducible nitric oxide synthase in aged murine lungs to endotoxic stress*. Ann Thorac Surg 2004; 77(4):1222-1227). Since NO from eNOS increases mitochondrial number in skeletal muscle, this might reverse aging. (Brown G C. *NO says YES to mitochondria*. Science 2003; 299:838-839.) Therefore, periodic acceleration alone and with caloric restriction as an additive or synergistic effect might favorably modify the ageing process.

N. Sjogren's Syndrome

Sjogren's syndrome is marked by xeropthalmia (dry eyes) and xerostomia (dry mouth) due to lymphocytic infiltrates of lacrimal and salivary glands. It may occur alone or in association with several other autoimmune diseases. The clinical features involve a wide variety of organs, including skin, eyes, oral cavity and salivary glands, and systems, including nervous, musculoskeletal, genitourinary and vascular. The dryness symptoms can be found in a number of other disorders including rheumatoid arthritis, systemic lupus erythematosus, scieroderma, primary biliary cirrhosis, and other rheumatic disorders. (Rehman H U. *Sjogren's syndrome*. Yonsei Med J 2003; 44(6):947-954.) Suppression of tumor necrosis factor alpha with cepharanthine, an anti-inflammatory, pro-apoptotic anti-tumorigenesis drug halts induction of matrix metalloproteinase 9 thereby preventing destruction of acinar tissue in the salivary glands of patients with Sjogren's syndrome. (Azuma M, Aota K, Tamatani T et al. *Suppression of tumor necrosis factor alpha-induced matrix metalloproteinase 9 production in human salivary gland acinar cells by cepharanthine occurs via down-regulation of nuclear factor kappaB: a possible therapeutic agent for preventing the destruction of the acinar structure in the salivary glands of Sjogren's syndrome patients*. Arthritis Rheum 2002; 46(6): 1585-1594) Periodic acceleration through activation of eNOS with subsequent NO release has an anti-inflammatory, pro-apoptotic action through suppression of nuclear factor kappa beta which in turn inhibits tumor necrosis factor alpha. Therefore, it has a place in management of Sjogren's syndrome.

O. Lyme Disease

The Lyme disease agent, *Borrelia burgdorferi*, a spirochete, causes infection by migration through tissues, adhesion to host cells, and evasion of immune clearance. The infection is introduced by a tick bite and cause a skin rash and persistent flu-like symptoms and fever in the summer. If inadequately treated, arthritis, cardiac arrhythmia marked by heart block, facial nerve palsy, meningitis, polyneuropathy and encepalopathy may occur. (Steere A C, Coburn J, Glickstein L. *The emergence of Lyme disease*. J Clin Invest 2004; 113(8):1093-1101.) The systemic symptoms of Lyme disease are due in part to activation of nuclear factor kappa beta with intense inflammatory cytokine expression with inflammation of microglia. (Ebnet K, Brown K D, Siebenlist U K et al. *Borrelia burgdorferi activates nuclear factor-kappa B and is a potent inducer of chemokine and adhesion molecule gene expression in endothelial cells and fibroblasts*. J Immunol 1997; 158(7):3285-3292; Rasley A, Anguita J, Marriott I. *Borrelia burgdorferi induces inflammatory mediator production by murine microglia. J Neuroimmunol* 2002; 130(1-2): 22-31.) In the acute phase of Lyme disease, periodic acceleration is contraindicated because nitric oxide from eNOS could suppress the host's immuno-defense mechanisms. But in the chronic phase of Lyme disease, periodic acceleration diminishes constitutional and local symptoms in the central nervous system, heart and joints in conjunction with antibiotics.

P. Gulf War Syndrome

The Gulf War syndrome consists of multisymptom illnesses characterized by persistent pain, fatigue, and cognitive symptoms that have been reported by many Gulf War veterans. Vaccinations against biological warfare using pertussis were utilized as an adjuvant in such patients. This could trigger neurodegeneration through induction of interleukin-1beta secretion in the brain. Particular susceptibility for IL-1beta secretion and potential distant neuronal damage could provide an explanation for the diversity of the symptoms. The symptoms in many of these patients are similar to the chronic fatigue syndrome and those with severe fatiguing illness have shown plasma immunological abnormalities but not as a universal finding. No measurements have been made of inflammatory cytokines in the cerebrospinal fluid where detection of pathology would be more likely to occur. (Donta S T, Clauw D J, Engel C C, Jr. et al. *Cognitive behavioral therapy and aerobic exercise for Gulf War veterans' illnesses: a randomized controlled trial*. JAMA 2003; 289(11):1396-1404; Tournier J N, Jouan A, Mathieu J et al. *Gulf war syndrome: could it be triggered by biological warfare-vaccines using pertussis as an adjuvant?* Med Hypotheses 2002; 58(4):291-292; Zhang Q, Zhou X D, Denny T et al. *Changes in immune parameters seen in Gulf War veterans but not in civilians with chronic fatigue syndrome*. Clin Diagn Lab Immunol 1999; 6(1):6-13; Everson M P, Shi K, Aldridge P et al. *Immunological responses are not abnormal in symptomatic Gulf War veterans*. Ann NY Acad Sci 2002; 966:327-342.)

Nitric oxide released from eNOS with periodic acceleration has a potent anti-inflammatory action through suppression of nuclear factor kappa beta. Perodic acceleration has been utilized in the treatment of fibromyalgia and chronic fatigue syndrome, entities with symptoms similar to those in the Gulf War syndrome. The dramatic improvement in symptoms of fibromyalgia and chronic fatigue syndrome was attributed to suppression of an inflammatory process in the brain. (Sackner M A, Gummels E M, Adams J A. *Say NO to fibromyalgia and chronic fatigue syndrome: an alternative and complementary therapy to aerobic exercise*. Med Hypotheses 2004; 63(1):118-123.) However, the cognitive improvement might also have been due to nitric oxide from eNOS enhancing long-term potentiation of frontalstriatal synapses that deal with memory and learning. (O'Dell T J, Huang P L, Dawson T M et al. *Endothelial NOS and the blockade of LTP by NOS inhibitors in mice lacking neuronal NOS*. Science 1994; 265(5171):542-546.)

In summary, periodic acceleration is indicated in treatment of the Gulf War syndrome.

Q. Miscellaneous Pulmonary Effects

Through the action of nitric oxide expressed from activation of eNOS, periodic acceleration improves mucociliary clearance, increases pulmonary surfactant productions and minimizes the volutrauma and barotrauma of positive pressure mechanical ventilation. Nitric oxide improves nasal mucociliary clearance by increasing ciliary beat frequency. (Runer T, Lindberg S. *Ciliostimulatory effects mediated by nitric oxide*. Acta Otolaryngol 1999; 119(7):821-825.) Unpublished experiments in our laboratory indicate that periodic acceleration through NO release from eNOS increases tracheal mucous velocity over baseline in conscious sheep and after administration of elastin, which is a potent suppressant of mucociliary clearance. Therefore, treatment with periodic acceleration is indicated in medical conditions associated with production of excessive bronchopulmonary and nasal secretions such as cystic fibrosis, bronchial asthma, chronic bronchitis and chronic sinusitis. Periodic acceleration should be helpful in shortening duration of the mucous surface. Further, constitutional symptoms are alleviated by NO suppression of nuclear factor kappa beta activity that directs inflammatory cytokine production. Physiological concentration as those released from eNOS stimulate pulmonary surfactant production and therefore periodical acceleration is indicated in the management of the adult and infant respiratory distress syndrome as well as SARS. (Sun P, Wang J, Mehta P et al. *Effect of nitric oxide on lung surfactant secretion*. Exp Lung Res 2003; 29(5):303-314.) Since pulmonary injury from mechanical ventilation is due to inflammation owing to activation of nuclear factor kappa beta, periodic acceleration through release of NO that blocks nuclear factor kappa beta activity can serve in prophylactic and therapeutic roles. (Uhlig U, Fehrenbach H, Lachmann R A et al. *Phosphoinositide 3-OH kinase inhibition prevents ventilation-induced lung cell activation*. Am J Respir Crit Care Med 2004; 169(2):201-208.)

R. Corticosteroid Resistance

Asthma patients who respond poorly or are resistance to the action of corticosteroids constitute slight less than 5% of 20 million patients for a total of about 1 million patients. (Adcock I M, Lane S J. *Corticosteroid-insensitive asthma: molecular mechanisms*. J Endocrinol 2003; 178(3):347-355.) Corticosteroid therapy resistance is a common indication for surgery in inflammatory bowel disease, with as many as 50% of patients with Crohn's disease and approximately 20% of patients with ulcerative colitis requiring surgery in their lifetime. One of the major causes of resistance is constitutive epithelial activation of proinflammatory mediators, including nuclear factor kappa B, resulting in inhibition of glucocorticoid receptor transcriptional activity. (Farrell R J, Kelleher D. *Glucocorticoid resistance in inflammatory bowel disease*. J Endocrinol 2003; 178(3):339-346.) Periodic acceleration by releasing NO from eNOS suppresses nuclear factor kappa beta activity and can used as a stand-alone therapy in patients with corticosteroid resistance asthma and inflammatory bowel disease.

S. Chronic Otitis Media

The chronic inflammation seen in some chronic otitis media patients appears to be due to lipopolysaccharide activating adhesion molecule receptors and nuclear factor kappa beta followed by release of IL-8. Since periodic acceleration releases NO from eNOS with subsequent suppression of nuclear factor kappa beta activity and IL-8, it can be utilized to treat patients with chronic otitis media. (Barrett T Q, Kristiansen L H, Ovesen T. *NF-kappaB in cultivated middle ear epithelium*. Int J Pediatr Otorhinolaryngol 2003; 67(8):895-903.)

T. Nail Growth and Nail Brittleness

In several patients that were chronically treated with periodic acceleration, nail growth was more rapid and nail brittleness improved. Presumably, this was related to increased blood supply to the nail bed. Therefore, periodic acceleration has a role in nail regeneration.

U. Cell Free Hemoglobin Transfusions

Hemoglobin-based oxygen carriers are being developed for use in blood replacement therapies, either for perioperative hemodilution or for resuscitation from hemorrhagic blood loss. There is a high demand for these products because of risks associated with blood transfusions and pending worldwide blood shortages. The primary adverse effect for the majority of cross-linked or polymerized cell free hemoglobin products is increased vascular resistance to blood flow. (Vandegriff K D. *Haemoglobin-based oxygen carriers*. Expert Opin Investig Drugs 2000; 9(9):1967-1984.) This side effect of cell free hemoglobin is a serious one and is due to hemoglobin scavenging nitric oxide from eNOS that renders the transfusion recipient nitric oxide deficient. Periodic acceleration through release of increased nitric oxide from eNOS can be used to prevent or treat the NO deficit.

V. Nuclear Weapons and "Dirty Bombs"

A major threat facing the world today is the possibility of a nuclear terrorist attack through a conventional nuclear weapon or a "dirty bomb" (combination of coventional explosive and nuclear material) or through an attack on a nuclear power plant site. Some deaths from an explosion would result from direct contact with the explosive and debris but the majority of early deaths would result from infections related to bone marrow suppression of neutrophils. Radiation to the abdomen can produce acute enteritis characterized by diarrhea and chronic enteropathy (hemorrhage and ulceration) which leads to progressively reduced mobility. Fistulas, strictures and malabsorption are potentially life threatening. Tumor necrosis factor alpha and IL-6 contribute significantly to leukemias and radiation pneumonitis. Because radiation-induced vascular injury precedes the tissue damage, vascular injury is regarded as crucial in the pathogenesis of tissue damage. Radiation injury is marked by activation of adhesion molecules that promote leukocyte infiltration of normal tissue. The stress of radiation activated nuclear factor kappa beta in turn promotes activation of adhesion molecules. The inflammatory mediators activated in radiation injury are regulated by nuclear factor kappa beta, the key gene directing the inflammatory response. (Linard C, Marquette C, Mathieu J et al. *Acute induction of inflammatory cytokine expression after gamma-irradiation in the rat: effect of an NF-kappaB inhibitor*. Int J Radiat Oncol Biol Phys 2004; 58(2):427-434; Quarmby S, Kumar P, Kumar S. *Radiation-induced normal tissue injury: role of adhesion molecules in leukocyte-endothelial cell interactions*. Int J Cancer 1999; 82(3):385-395.) Periodic acceleration through NO released from eNOS suppresses nuclear factor kappa beta activity and the inflammatory cytokines. Therefore, it serves ro treat radiation injuries.

The invention is not limited by the embodiments described above which are presented as examples only but can be modified in various ways within the scope of protection defined by the appended patent claims. Thus, while there have shown and described and pointed out fundamental novel features of the invention as applied to a preferred embodiment thereof, it will be understood that various omissions and substitutions and changes in the form and details of the devices illustrated, and in their operation, may be made by those skilled in the art without departing from the spirit of the invention. For example, it is expressly intended that all combinations of those elements and/or method steps which perform substantially the same function in substantially the same way to achieve the same results are within the scope of the invention. Moreover, it should be recognized that structures and/or elements and/or method steps shown and/or described in connection with any disclosed form or embodiment of the invention may be incorporated in any other disclosed or described or suggested form or embodiment as a general matter of design choice. It is the intention, therefore, to be limited only as indicated by the scope of the claims appended hereto.

What is claimed is:

1. A motion platform for providing periodic acceleration to a subject, comprising:

a box frame providing a foundation of the motion platform, said box frame having four wheel tracks located substantially at the four corners of the top portion of the box frame;

a drive module having four track wheels located substantially at the four corners of the top portion of the drive module, wherein said track wheels extend from the top portion of the drive module and rest in the wheel tracks of the box frame, whereby the drive module sits within the box frame and is operably movable relative to said box frame;

a support connected to said drive module, said support comprising a planar surface for supporting the subject, said planar surface having a head end and a foot end; and said drive module comprises a displacement module for providing periodic acceleration to the subject by moving the drive module in a line parallel to the planar surface of the support, and the periodic acceleration is alternately in the direction of the head end, and the foot end, of the planar surface, the movement of the drive module having a force in a range of about 0.1 g to about 0.4 g such that the motion platform adds pulses to the fluid filled channels of the body of the subject, the displacement module being connected to said box frame only through said drive module, whereby the displacement module is not directly connected to said box frame.

2. The motion platform of claim 1, wherein the movement of the drive module is substantially sinusoidal.

3. The motion platform of claim 1, wherein the displacement of the drive module is about 1 cm to 5 cm.

4. The motion platform of claim 1, wherein the displacement of the drive module is about 2.5 cm.

5. The motion platform of claim 1, wherein the speed of the drive module is about 120 to 160 cycles per minute.

6. The motion platform of claim 1, wherein the speed of the drive module is about 140 cycles per minute.

7. The motion platform of claim 1, wherein the movement of the drive module has a force in a range of about 0.15 g to about 0.2 g.

8. The motion platform of claim 1, wherein the motion platform is preset based on the size of the subject who will use the motion platform.

9. The motion platform of claim 8, wherein the subject is obese and the motion platform is preset such that the movement of the drive module has a force of about 0.17 g.

10. The motion platform of claim 9, wherein the subject has normal body weight and the motion platform is preset such that the movement of the drive module has a force of about 0.17 g.

11. The motion platform of claim 1, wherein the motion platform also serves as a bed.

12. The motion platform of claim 1, wherein the motion platform also serves as a sofa.

13. The motion platform of claim 1, wherein the planar surface of the support can fit more than one subject.

14. A motion platform for providing periodic acceleration to a subject, comprising:

a box frame providing a foundation of the motion platform;

a drive module adjoining said box frame, said drive module operably movable relative to said box frame; and a support connected to said drive module, said support comprising a planar surface for supporting the subject, said planar surface having a head end and a foot end;

wherein said drive module comprises a displacement module for inducing periodic acceleration to the subject by moving in a line parallel to the planar surface of the support, and the periodic acceleration is alternately in the direction of the head end, and the foot end, of the planar surface, the movement of the drive module having a force in a range of about 0.1 g to about 0.4 g such that the motion platform adds pulses to the fluid filled channels of the body of the subject, the displacement module being connected to said box frame only through said drive module, whereby the displacement module is not directly connected to said box frame.

15. The motion platform of claim 14, wherein the provided periodic acceleration is used as a stand-alone treatment or in conjunction with other therapeutic and/or preventative modalities.

16. The motion platform of claim 14, wherein the provided periodic acceleration is used to treat and/or to prevent cancers in tissues of the subject.

17. The motion platform of claim 14, wherein the provided periodic acceleration causes release of nitric oxide from the vascular endothelium of the subject though activation of endothelial nitric oxide synthase (eNOS) which in turn suppresses nuclear factor kappa beta.

18. The motion platform of claim 14, wherein the provided periodic acceleration serves as a means for preconditioning, conditioning and/or postconditioning tissues of the body of the subject.

19. The motion platform of claim 18, wherein treatment with periodic acceleration before, during, or after athletic performance prevents and/or treats tissue damage, reduces systemic stress, increases athletic performance, and/or prevents/treats any of the problems caused by strenuous athletic activity.

20. The motion platform of claim 18, wherein regular treatment with periodic acceleration as a regimen for the athlete prevents and/or treats tissue damage, reduces systemic stress, increases athletic performance, and/or prevents/treats any of the problems caused by strenuous athletic activity.

21. The motion platform of claim 18, wherein pretreatment with periodic acceleration improves athletic performance by preconditioning a body tissue of the athlete.

22. The motion platform of claim 18, wherein pretreatment with periodic acceleration mitigates skeletal muscular cramps and/or helps prevent muscle strains during an athletic event.

23. The motion platform of claim 18, wherein pretreatment with periodic acceleration mitigates and/or helps prevent delayed onset muscular soreness (DOMS) and involuntary muscle cramps and spasms immediately following the athletic event and/or delayed until the sleeping hours.

24. The motion platform of claim 18, wherein pretreatment with periodic acceleration is used to treat exercise-induced bronchospasm in an athlete.

25. The motion platform of claim 18, wherein pretreatment with periodic acceleration helps to reduce and/or prevent susceptibility of athletes to viral and bacterial infections.

26. The motion platform of claim 18, wherein the pretreatment, treatment, and/or post-treatment with periodic acceleration treats or prevents cramps, aches, soreness, spasms, and other maladies brought on by exercise and/or other athletic activity.

27. The motion platform of claim 14, wherein treatment using periodic acceleration assists or reduces the use of corticosteroids and non-steriodal anti-inflammatory drugs (NSAJDs) in management of pain, injury, muscle soreness, strains, and contusions in athletes.

28. The motion platform of claim 14, wherein the provided periodic acceleration causes release of nitric oxide from the vascular endothelium of the subject though activation of endothelial nitric oxide synthase (eNOS) that in turn scavenges reactive oxygen species thereby diminishing or eliminating oxidative stress.

29. The motion platform of claim 14, wherein the periodic acceleration provided by a motion platform to the subject causes release of nitric oxide from the vascular endothelium of the patient through activation of endothelial nitric oxide synthase (eNOS) which in turn suppresses the activity of inducible nitric oxide synthase (iNOS).

30. The motion platform of claim 29, wherein the periodic acceleration treats and/or prevents cramps, aches, soreness, spasms, and the like at least because the suppression of nuclear factor kappa beta diminishes IL-1beta, IL-6, tumor necrosis factor and other inflammatory cytokines and adhesion molecules.

31. The motion platform of claim 14, wherein treatments of periodic acceleration are used to ameliorate metabolic syndrome or to improve skeletal muscle pathology associated with the cachexia of COPD and cancers in weight control of the subject.

32. The motion platform of claim 14, wherein periodic acceleration is used to prevent ventricular remodeling.

33. The motion platform of claim 14, wherein periodic acceleration is used to treat and/or prevent complications from coronary bypass surgery.

34. The motion platform of claim 14, wherein periodic acceleration is used to treat and/or prevent obstructive sleep apnea syndrome commonly observed in patients with coronary artery disease.

35. The motion platform of claim 14, wherein periodic acceleration is used to treat and/or prevent cognitive deficits, learning deficits, and/or behavioral abnormalities in early cognitive impairment.

36. The motion platform of claim 14, wherein periodic acceleration is used to treat and/or prevent Alzheimer's disease, vascular dementias, Parkinson's disease, amyotrophic lateral sclerosis, Huntington's chorea, and Wilson's disease.

37. The motion platform of claim 14, wherein periodic acceleration is used to treat and/or prevent cardiac allograft vasculopathy.

38. The motion platform of claim 14, wherein periodic acceleration is used to promote angiogenesis in ischemic tissues.

39. The motion platform of claim 14, wherein periodic acceleration is used to manage hereditary hemorrhagic telangiectasia.

40. The motion platform of claim 14, wherein periodic acceleration is used to treat and/or prevent migraine.

41. The motion platform of claim 14, wherein periodic acceleration is used to treat the inflammation attendant with prion diseases.

42. The motion platform of claim 14, wherein periodic acceleration is used to manage the aging process.

43. The motion platform of claim 14, wherein periodic acceleration is used to manage Sjogren's syndrome.

44. The motion platform of claim 14, wherein periodic acceleration is used to manage the chronic phase of Lyme disease.

45. The motion platform of claim 14, wherein periodic acceleration is used to improve mucocilary clearance and surfactant production, and to minimize lung damage associated with usual positive pressure mechanical ventilation.

46. The motion platform of claim 14, wherein periodic acceleration is used to treat patients who have corticosteroid resistance and asthma or corticosteroid resistance and inflammatory bowel disease.

47. The motion platform of claim 14, wherein periodic acceleration is used to treat chronic otitis media.

48. The motion platform of claim 14, wherein periodic acceleration is used to in conjunction with cell free hemoglobin transfusion in order to treat and/or prevent a nitric oxide deficit.

49. A method of medical treatment of a subject comprising the step of:

providing periodic acceleration to a body of the subject in order to externally and non-invasively add pulses to the body's fluid-filled channels over the body's own pulse;

wherein the periodic acceleration is provided by a motion platform comprised of a support on a drive module held by, and operably movable relative to, a box frame, wherein the subject is set on the support, and wherein the drive module is moved relative to the box frame to provide periodic acceleration to the body of the subject by a displacement module connected to said box frame only through said drive module, whereby the displacement module is not directly connected to said box frame, said displacement module providing periodic acceleration to the subject by moving the drive module in a line parallel to a planar surface of the support, and the periodic acceleration is alternately in the direction of the head end, and the foot end, of the planar surface, the movement of the drive module having a force in a range of about 0.1 g to about 0.4 g such that the motion platform adds pulses to the fluid filled channels of the body of the subject.

50. The method of claim 49, wherein a motor secured to said box frame moves the drive module to provide the periodic acceleration of the subject.

51. The method of claim 49, wherein the provided periodic acceleration is used to treat and/or to prevent cancers in tissues of the subject.

52. The method of claim 49, wherein the provided periodic acceleration serves as a means for preconditioning, conditioning and/or postconditioning tissues of the body of the subject.

53. The method of claim 52, wherein treatment with periodic acceleration before, during, or after athletic performance prevents and/or treats tissue damage, reduces systemic stress, increases athletic performance, and/or prevents/treats any of the problems caused by strenuous athletic activity.

54. The method of claim 52, wherein regular treatment with periodic acceleration as a regimen for the athlete prevents and/or treats tissue damage, reduces systemic stress, increases athletic performance, and/or prevents/treats any of the problems caused by strenuous athletic activity.

55. The method of claim 52, wherein pretreatment with periodic acceleration improves athletic performance by preconditioning a body tissue of the athlete.

56. The method of claim 52, wherein pretreatment with periodic acceleration mitigates skeletal muscular cramps and/or helps prevent muscle strains during an athletic event.

57. The method of claim 52, wherein pretreatment with periodic acceleration mitigates and/or helps prevent delayed onset muscular soreness (DOMS) and involuntary muscle cramps and spasms immediately following the athletic event and/or delayed until the sleeping hours.

58. The method of claim 52, wherein pretreatment with periodic acceleration is used to treat exercise-induced bronchospasm in an athlete.

59. The method of claim 52, wherein pretreatment with periodic acceleration helps to reduce and/or prevent susceptibility of athletes to viral and bacterial infections.

60. The method of claim 52, wherein the pretreatment, treatment, and/or post-treatment with periodic acceleration treats or prevents cramps, aches, soreness, spasms, and other maladies brought on by exercise and/or other athletic activity.

61. The method of claim 49, wherein treatment using periodic acceleration assists or reduces the use of corticosteroids and non-steriodal anti-inflammatory drugs (NSAIDs) in management of pain, injury, muscle soreness, strains, and contusions in athletes.

62. The method of claim 49, wherein the provided periodic acceleration causes release of nitric oxide from the vascular endothelium of the subject though activation of endothelial nitric oxide synthase (eNOS) that in turn scavenges reactive oxygen species thereby diminishing or eliminating oxidative stress.

63. The method of claim 49, wherein the periodic acceleration treats and/or prevents cramps, aches, soreness, spasms, and the like at least by diminishing any one of IL-1beta, JL-6, tumor necrosis factor or other inflammatory cytokines and adhesion molecules through suppression of nuclear factor kappa beta caused by activation of endothelial nitric oxide synthase (eNOS) which is caused by release of nitric oxide from the vascular endothelium of the patient.

64. The method of claim 49, wherein treatments of periodic acceleration are used to ameliorate metabolic syndrome or to improve skeletal muscle pathology associated with the cachexia of COPD and cancers in weight control of the subject.

65. The method of claim 49, wherein periodic acceleration is used to prevent ventricular remodeling.

66. The method of claim 65, wherein periodic acceleration is combined with drugs that stabilize cardiac mast cells and/or cardiac drugs that activate eNOS.

67. The method of claim 49, wherein periodic acceleration is used to treat and/or prevent complications from coronary bypass surgery.

68. The method of claim 49, wherein periodic acceleration is used to treat and/or prevent obstructive sleep apnea syndrome commonly observed in patients with coronary artery disease.

69. The method of claim 49, wherein periodic acceleration is used to treat and/or prevent cognitive deficits, learning deficits, and/or behavioral abnormalities in early cognitive impairment.

70. The method of claim 49, wherein periodic acceleration is used to treat and/or prevent Alzheimer's disease, vascular dementias, Parkinson's disease, amyotrophic lateral sclerosis, Huntington's chorea, and Wilson's disease.

71. The method of claim 49, wherein periodic acceleration is used to treat and/or prevent cardiac allograft vasculopathy.

72. The method of claim 49, wherein periodic acceleration is used to promote angiogenesis in ischemic tissues.

73. The method of claim 49, wherein periodic acceleration is used to manage hereditary hemorrhagic telangiectasia.

74. The method of claim 49, wherein periodic acceleration is used to treat and/or prevent migraine.

75. The method of claim 49, wherein periodic acceleration is used to treat the inflammation attendant with prion diseases.

76. The method of claim 49, wherein periodic acceleration is used to manage the aging process.

77. The method of claim 49, wherein periodic acceleration is used to manage Sjogren's syndrome.

78. The method of claim 49, wherein periodic acceleration is used to manage the chronic phase of Lyme disease.

79. The method of claim 78, wherein periodic acceleration is combined with antibiotics.

80. The method of claim 49, wherein periodic acceleration is used to improve mucocilary clearance and surfactant production, and to minimize lung damage associated with usual positive pressure mechanical ventilation.

81. The method of claim 49, wherein periodic acceleration is used to treat patients who have corticosteroid resistance and asthma or corticosteroid resistance and inflammatory bowel disease.

82. The method of claim 49, wherein periodic acceleration is used to treat chronic otitis media.

83. The method of claim 49, wherein periodic acceleration is used to in conjunction with cell free hemoglobin transfusion in order to treat and/or prevent a nitric oxide deficit.

* * * * *